United States Patent
Ren et al.

(10) Patent No.: US 10,876,953 B2
(45) Date of Patent: Dec. 29, 2020

(54) SYSTEM AND METHOD FOR LABEL SELECTION

(71) Applicant: Becton, Dickinson and Company, Franklin Lakes, NJ (US)

(72) Inventors: Ran Ren, San Jose, CA (US); Heng Xu, Castro Valley, CA (US); Maria Semyonova, Los Gatos, CA (US); Maria Jaimes, Los Altos, CA (US); Alan M. Stall, Encinitas, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 412 days.

(21) Appl. No.: 15/744,030

(22) PCT Filed: Jul. 13, 2016

(86) PCT No.: PCT/US2016/042083
§ 371 (c)(1),
(2) Date: Jan. 11, 2018

(87) PCT Pub. No.: WO2017/011549
PCT Pub. Date: Jan. 19, 2017

(65) Prior Publication Data
US 2018/0231452 A1   Aug. 16, 2018

Related U.S. Application Data

(60) Provisional application No. 62/192,963, filed on Jul. 15, 2015, provisional application No. 62/192,986, filed on Jul. 15, 2015.

(51) Int. Cl.
*G01N 15/14* (2006.01)
*C12Q 1/04* (2006.01)
*G01N 15/10* (2006.01)

(52) U.S. Cl.
CPC .......... *G01N 15/1425* (2013.01); *C12Q 1/04* (2013.01); *G01N 15/1459* (2013.01); *G01N 2015/1006* (2013.01); *G01N 2015/1477* (2013.01)

(58) Field of Classification Search
None
See application file for complete search history.

(56) References Cited

U.S. PATENT DOCUMENTS

| | | |
|---|---|---|
| 4,704,891 A | 11/1987 | Recktenwald et al. |
| 4,777,133 A | 10/1988 | Picciolo et al. |
| 4,845,653 A | 7/1989 | Conrad et al. |
| 4,857,451 A | 8/1989 | Schwartz |
| 5,093,234 A | 3/1992 | Schwartz |
| 5,599,932 A | 2/1997 | Bieniarz et al. |
| 5,627,040 A | 5/1997 | Bierre et al. |
| 5,658,751 A | 8/1997 | Yue et al. |
| 5,739,000 A | 4/1998 | Bierre et al. |
| 5,784,162 A | 7/1998 | Cabib et al. |
| 5,795,727 A | 8/1998 | Bierre et al. |
| 5,962,238 A | 10/1999 | Sizto et al. |
| 6,014,904 A | 1/2000 | Lock |
| 6,897,954 B2 | 5/2005 | Bishop et al. |
| 6,944,338 B2 | 9/2005 | Lock et al. |
| 7,674,598 B2 | 3/2010 | Paul et al. |
| 7,932,503 B2 | 4/2011 | Parks et al. |
| 8,116,984 B2 | 2/2012 | Davis et al. |
| 8,309,306 B2 | 11/2012 | Nolan et al. |
| 8,364,418 B2 | 1/2013 | Davis et al. |
| 8,380,541 B1 | 2/2013 | Holmes |
| 8,538,774 B2 | 9/2013 | Michelson et al. |
| 8,731,844 B2 | 5/2014 | Herzenberg et al. |
| 10,215,685 B2 | 2/2019 | Zigon et al. |
| 10,235,429 B2 | 3/2019 | Meehan et al. |
| 10,502,678 B2 | 12/2019 | Kapinsky |
| 2004/0119974 A1 | 6/2004 | Bishop et al. |
| 2008/0240988 A1 | 10/2008 | Wakamiya et al. |
| 2009/0142231 A1 | 6/2009 | Shibuya et al. |
| 2010/0256943 A1 | 10/2010 | Donnenberg et al. |
| 2011/0282870 A1 | 11/2011 | Herzenberg et al. |
| 2012/0245889 A1 | 9/2012 | Zhu et al. |
| 2013/0078621 A1 | 3/2013 | Nolan et al. |
| 2013/0323825 A1 | 12/2013 | Sekino et al. |

(Continued)

FOREIGN PATENT DOCUMENTS

| | | |
|---|---|---|
| EP | 1431745 A1 | 6/2004 |
| EP | 1836557 A2 | 9/2007 |

(Continued)

OTHER PUBLICATIONS

Bauer et al. (eds.), Clinical Flow Cytometry: Principles and Applications, Williams & Wilkins (1993).

(Continued)

*Primary Examiner* — Michael L Borin
(74) *Attorney, Agent, or Firm* — Khin K. Chin; Bret E. Field; Bozicevic, Field & Francis LLP

(57) ABSTRACT

Methods and systems for performing a flow cytometry experiment can include evaluating one or more assignments of labels to a plurality of markers. Evaluating assignments of labels can include evaluating condition numbers for at least one spillover matrix. The method can further include selecting labels based at least in part on the evaluation of condition numbers. Methods and systems for performing a flow cytometry experiment can also include inputting data regarding markers, cell populations, labels, and cytometer configuration for a flow cytometry experiment, assigning labels to at least some of the markers, and running the flow cytometry experiment.

15 Claims, 26 Drawing Sheets

(56) References Cited

U.S. PATENT DOCUMENTS

| | | | |
|---|---|---|---|
| 2014/0309782 A1 | 10/2014 | Sharpe et al. |
| 2015/0140577 A1 | 5/2015 | Li et al. |
| 2016/0025621 A1 | 1/2016 | Kapinsky |
| 2016/0123980 A1 | 5/2016 | Evans et al. |
| 2018/0231452 A1 | 8/2018 | Ren et al. |
| 2020/0132594 A1 | 4/2020 | Kapinsky |

FOREIGN PATENT DOCUMENTS

| | | |
|---|---|---|
| EP | 2 711 713 | 3/2014 |
| EP | 2 843 418 | 3/2015 |
| EP | 2972213 B1 | 1/2016 |
| EP | 2347352 B1 | 11/2019 |
| FR | 2 994 740 A1 | 2/2014 |
| WO | WO 2013/134491 | 9/2013 |
| WO | WO 2014/029743 | 2/2014 |
| WO | WO 2014/144826 A1 | 9/2014 |
| WO | WO2014188170 A1 | 11/2014 |

OTHER PUBLICATIONS

Biosciences, B.D. "An Introduction to Compensation for Multicolor Assays on Digital Flow Cytometers." BDbiosciences.com (2009).

Biosciences, B.D. "Introduction to Flow Cytometry: A learning guide." *Manual Part* 1 (2000).

Jaroszeski et al. (eds.), Flow Cytometry Protocols, Methods in Molecular Biology No. 91, Humana Press (1997).

Landay et al. (eds.), Clinical Flow Cytometry, Annals of the New York Academy of Sciences vol. 677 (1993).

Ormerod (ed.), Flow Cytometry: A Practical Approach, Oxford Univ. Press (1997).

Pawley (ed.), Handbook of Biological Confocal Microscopy, 2nd Edition, Plenum Press (1989).

Shapiro, Howard M. *Practical flow cytometry*, 4th ed. John Wiley & Sons, 2003.

International Search Report for International Application No. PCT/US2015/014681 dated Apr. 15, 2015.

International Search Report and Written Opinion dated Oct. 20, 2016, received in PCT/US2016/042083, filed Jul. 13, 2016.

MY PANELS / BD SAMPLE PANEL: TREG / NO RULES / Describe Panel
BD SAMPLE PANEL: TREG / NO RULES

| Describe Panel | Define Markers | Define Populations | Choose Cytometer | Design Panel | Review Panel |

This tool help you quickly build reagent panels for your experiment. Simply follow the instruments and you will be able to build your panels in no time.

Name*
[BD Sample Panel: Treg / No Rules] — 401

Description
[An example of a panel designed using no rules] — 402

☒ CONTACT US
[Save] [Continue →]

MY PANELS / BD SAMPLE PANEL: TREG / NO RULES / Design Panel
BD SAMPLE PANEL: TREG / NO RULES

| Describe Panel | Define Markers | Define Populations | Choose Cytometer | Design Panel | Review Panel |

Co-expression

| Markers | Treg | Naïve Treg | CD8 Mem |
|---|---|---|---|
| CD3 | H | H | |
| CD4 | H | H | |
| CD127 | L | L | |
| CD25 | L | L | |
| CD45RA | | M | H |

441

Match the below Markers to Fluorochromes based on above Co-Expression Levels.

Markers: CD3, CD4, CD127, CD25, CD45RA, CD8

443

| | Fluorochromes | Laser | |
|---|---|---|---|
| CD45RA | × | BB515 | ○ Blue | 4 |
| CD4 | × | Alexa Fluor 647 | ○ Red | 3 |
| CD8 | × | APC | ○ Red | |
| | | PE | ○ Blue | |
| | | PE-Cy7 | ○ Blue | |
| CD127 | × | Alexa Fluor 488 | ○ Blue | 2 |
| CD3 | × | FITC | ○ Blue | |
| | | PerCP-Cy5.5 | ○ Blue | |
| CD25 | × | APC-Cy7 | ○ Red | 1 |
| | | Mismatch of Fluorochrome brightness and antigen resolution | | |
| | | PerCP | ○ Blue | |

442  444  446

Resolution Impact  436

Analyze Panel  445

◀ Back   Save   Continue ▶

✉ CONTACT US

MY PANELS / BD SAMPLE PANEL: TREG / NO RULES / Review Panel

BD SAMPLE PANEL: TREG / NO RULES

| Describe Panel | Define Markers | Define Populations | Choose Cytometer | Design Panel | Review Panel |

BD SAMPLE PANEL: TREG / NO RULES
Author: Demo bdbio
Last Modified: 05/19/2026 01:02 PM PST
Cytometer, Configuration: BD FACSCanto™/BDFACSCanto™ II, 4-Blue 2-Red
Target Species: Human
Description: An example of a panel designed using no rules Please review the grid below, select the Reagent and click the Exit button to complete work on this panel.

| Specificity | Fluorochrome | Catalog # | | Reagent Description | TDS |
|---|---|---|---|---|---|
| CD127 | FITC | ☑ 560549 | BD | Hu CD127 FITC hIL-7R-M21 100Tst | Download |
|  |  | ☐ 561697 | BD | Hu CD127 FITC hIL-7R-M21 25Tst | Download |
| CD3 | PerCP-Cy5.5 | ☑ 340948 | BD | CD3 PerCP-Cy5.5 SK7 ASR | Download |
|  |  | ☐ 340949 | BD | CD3 PerCP-Cy5.5 SK7 50 Tests RUO/GMP | Download |
| CD4 | PE | ☑ 340670 | BD | CD4 PE SK3 ASR | Download |
|  |  | ☐ 347327 | BD | CD4 PE SK3 100 Tests RUO/GMP | Download |
|  |  | ☐ 550630 | BD | Hu/NHP CD4 PE L200 50Tst | Download |
|  |  | ☐ 555347 | BD | Hu CD4 PE RPA-T4 100Tst | Download |
|  |  | ☐ 556616 | BD | Hu/NHP CD4 PE RPA-T4 50Tst | Download |
|  |  | ☐ 561843 | BD | Hu CD4 PE RPA-T4 25Tst | Download |
|  |  | ☐ 561844 | BD | Hu CD4 PE RPA-T4 500Tst | Download |
| CD45RA | APC | ☑ 550855 | BD | Hu CD45RA APC HI100 100Tst | Download |
|  |  | ☐ 561210 | BD | Hu/NHP CD45RA APC 5H9 50Tst | Download |
|  |  | ☐ 561884 | BD | Hu CD45RA APC HI100 25Tst | Download |
| CD8 | PE-Cy7 | ☑ 557746 | BD | Hu CD8 PE-Cy7 RPA-T8 100Tst | Download |
|  |  | ☐ 557750 | BD | Hu/NHP CD8 PE-Cy7 RPA-T8 50Tst | Download |
|  |  | ☐ 560917 | BD | Hu CD8 PE-Cy7 RPA-T8 25Tst | Download |
| CD25 | PerCP | No matches available | | | |

[Export]

FIG. 4J

|  | CD3 | CD4 | CD8 | CD11c | CD14 | CD16 | CD19 | CD45 | CD56 |
|---|---|---|---|---|---|---|---|---|---|
| Lymph Helper | X | X |  |  |  |  |  | X |  |
| Lymph Cytotoxic | X |  | X |  |  |  |  | X |  |
| Lymph B Cell |  |  |  |  |  |  | X | X |  |
| Lymph NK |  |  |  |  |  | X |  | X | X |
| Monocyte |  | X |  | X | X | X |  | X |  |
| Dendritic |  |  | X | X |  | X |  | X |  |
|  | L1 L2 L3 L4 L5 L6 L7 L8 L9 L10 L11 L12 L13 | L1 L2 L3 L4 L5 L6 L7 L8 L9 L10 L11 L12 L13 | L1 L2 L3 L4 L5 L6 L7 L8 L9 L10 L11 L12 L13 | L1 L2 L3 L4 L5 L6 L7 L8 L9 L10 L11 L12 L13 | L1 L2 L3 L4 L5 L6 L7 L8 L9 L10 L11 L12 L13 | L1 L2 L3 L4 L5 L6 L7 L8 L9 L10 L11 L12 L13 | L1 L2 L3 L4 L5 L6 L7 L8 L9 L10 L11 L12 L13 | L1 L2 L3 L4 L5 L6 L7 L8 L9 L10 L11 L12 L13 | L1 L2 L3 L4 L5 L6 L7 L8 L9 L10 L11 L12 L13 |

FIG. 5A

|  | CD3 | CD4 | CD8 | CD11c | CD14 | CD16 | CD19 | CD45 | CD56 |
|---|---|---|---|---|---|---|---|---|---|
| Lymph Helper | X | X | | | | | | | |
| Lymph Cytotoxic | X | | X | | | | | | |
| Lymph B Cell | | | | | | | X | | |
| Lymph NK | | | | | | X | | X | X |
| Monocyte | | X | | X | X | X | | X | |
| Dendritic | | | X | X | | X | | X | |
| L1 L2 L3 L4 L5 L6 L7 L8 L9 L10 L11 L12 L13 | *L1 L2 L3 L4 L5 L6 L7 L8 L9 L10 L11 L12 L13* | *L1 L2 L3 L4 L5 L6 L7 L8 L9 L10 L11 L12 L13* | *L1 L2 L3 L4 L5 L6 L7 L8 L9 L10 L11 L12 L13* | *L1 L2 L3 L4 L5 L6 L7 L8 L9 L10 L11 L12 L13* | *L1 L2 L3 L4 L5 L6 L7 L8 L9 L10 L11 L12 L13* | *L1 L2 L3 L4 L5 L6 L7 L8 L9 L10 L11 L12 L13* | *L1 L2 L3 L4 L5 L6 L7 L8 L9 L10 L11 L12 L13* | *L1 L2 L3 L4 L5 L6 L7 L8 L9 L10 L11 L12 L13* |

*FIG. 5B*

|  | CD3 | CD4 | CD8 | CD11c | CD14 | CD16 | CD19 | CD45 | CD56 |
|---|---|---|---|---|---|---|---|---|---|
| Lymph Helper | X | X | | | | | | | |
| Lymph Cytotoxic | X | | X | | | | | | |
| Lymph B Cell | | | | | | | X | | |
| Lymph NK | | | | | | X | | | X |
| Monocyte | | X | | X | X | X | | X | |
| Dendritic | | | X | X | | X | | X | |
|  | L1 L3 L4 L7 L8 L9 L11 L13 | L2 L5 L6 10 L12 | L1 L3 L4 L7 L8 L9 L11 L13 | L2 L5 L6 10 L12 | L2 L5 L6 10 L12 | L2 L5 L6 10 L12 | L1 L3 L4 L7 L8 L9 L11 L13 | L2 L5 L6 10 L12 | L1 L3 L4 L7 L8 L9 L11 L13 |

FIG. 5C

| | CD3 | CD4 | CD8 | CD11c | CD14 | CD16 | CD19 | CD45 | CD56 |
|---|---|---|---|---|---|---|---|---|---|
| Lymph Helper | X | X | | | | | | X | |
| Lymph Cytotoxic | X | | X | | | | | X | |
| Lymph B Cell | | | | | | | X | X | |
| Lymph NK | | | | | | X | | X | X |
| Monocyte | | X | | X | X | X | | X | |
| *Dendritic* | | | *X* | *X* | | *X* | | *X* | |
| | *L1*<br>*L3*<br>*L4*<br>*L7*<br>*L8*<br>*L9*<br>*L11*<br>*L13* | *L2*<br>*L5*<br>*L6*<br>*10*<br>*L12* | *L1*<br>*L3*<br>*L4*<br>*L7*<br>*L8*<br>*L9*<br>*L11*<br>*L13* | *L2*<br>*L5*<br>*L6*<br>*10*<br>*L12* | *L2*<br>*L5*<br>*L6*<br>*10*<br>*L12* | *L2*<br>*L5*<br>*L6*<br>*10*<br>*L12* | *L1*<br>*L3*<br>*L4*<br>*L7*<br>*L8*<br>*L9*<br>*L11*<br>*L13* | *L2*<br>*L5*<br>*L6*<br>*10*<br>*L12* | *L1*<br>*L3*<br>*L4*<br>*L7*<br>*L8*<br>*L9*<br>*L11*<br>*L13* |

*FIG. 5D*

| | CD3 | CD4 | CD8 | CD11c | CD14 | CD16 | CD19 | CD45 | CD56 |
|---|---|---|---|---|---|---|---|---|---|
| Lymph Helper | X | X | | | | | | X | |
| Lymph Cytotoxic | X | | X | | | | | X | |
| Lymph B Cell | | | | | | | X | X | |
| Lymph NK | | | | | | X | | X | X |
| Monocyte | | X | | X | X | X | | X | |
| Dendritic | | | X | X | | X | | X | |
| | L3<br>L4<br>L7<br>L8<br>L9<br>L11<br>L13 | L2<br>L6 | L1 | L5<br>L10<br>L12 | L2<br>L6 | L5<br>L10<br>L12 | L3<br>L4<br>L7<br>L8<br>L9<br>L11<br>L13 | L5<br>L10<br>L12 | L3<br>L4<br>L7<br>L8<br>L9<br>L11<br>L13 |

*FIG. 5E*

| | CD3 | CD4 | CD8 | CD11c | CD14 | CD16 | CD19 | CD45 | CD56 |
|---|---|---|---|---|---|---|---|---|---|
| *Lymph Helper* | X | X | | | | | | X | |
| Lymph Cytotoxic | X | | X | | | | | X | |
| Lymph B Cell | | | | | | | X | X | |
| Lymph NK | | | | | | X | | X | X |
| Monocyte | | X | | X | X | X | | X | |
| Dendritic | | | X | X | | X | | X | |
| | *L3*<br>*L4*<br>*L7*<br>*L8*<br>*L9*<br>*L11*<br>*L13* | *L2*<br>*L6* | L1 | *L5*<br>*L10*<br>*L12* | L2<br>L6 | L5<br>L10<br>L12 | L3<br>L4<br>L7<br>L8<br>L9<br>L11<br>L13 | *L5*<br>*L10*<br>*L12* | L3<br>L4<br>L7<br>L8<br>L9<br>L11<br>L13 |

*FIG. 5F*

|  | CD3 | CD4 | CD8 | CD11c | CD14 | CD16 | CD19 | CD45 | CD56 |
|---|---|---|---|---|---|---|---|---|---|
| Lymph Helper | X | X | | | | | | X | |
| Lymph Cytotoxic | X | | X | | | | | X | |
| Lymph B Cell | | | | | | | X | X | |
| Lymph NK | | | | | | X | | X | X |
| Monocyte | | X | | X | X | X | | X | |
| Dendritic | | | X | X | | X | | X | |
|  | L4 | L6 | L1 | L5<br>L10 | L2 | L5<br>L10 | L3<br>L7<br>L8<br>L9<br>L11<br>L13 | L12 | L3<br>L7<br>L8<br>L9<br>L11<br>L13 |

FIG. 5G

| | CD3 | CD4 | CD8 | CD11c | CD14 | CD16 | CD19 | CD45 | CD56 |
|---|---|---|---|---|---|---|---|---|---|
| Lymph Helper | X | X | | | | | | X | |
| *Lymph Cytotoxic* | X | | X | | | | | X | |
| Lymph B Cell | | | | | | | X | X | |
| Lymph NK | | | | | | X | | X | X |
| Monocyte | | X | | X | X | X | | X | |
| Dendritic | | | X | X | | X | | X | |
| | *L4* | *L6* | *L1* | L5<br>L10 | *L2* | L5<br>L10 | L3<br>L7<br>L8<br>L9<br>L11<br>L13 | *L12* | L3<br>L7<br>L8<br>L9<br>L11<br>L13 |

*FIG. 5H*

|  | CD3 | CD4 | CD8 | CD11c | CD14 | CD16 | CD19 | CD45 | CD56 |
|---|---|---|---|---|---|---|---|---|---|
| Lymph Helper | X | X |  |  |  |  |  | X |  |
| Lymph Cytotoxic | X |  | X |  |  |  |  | X |  |
| Lymph B Cell |  |  |  |  |  |  | X | X |  |
| *Lymph NK* |  |  |  |  |  | X |  | X | X |
| Monocyte |  | X |  | X | X | X |  | X |  |
| Dendritic |  |  | X | X |  | X |  | X |  |
|  | *L4* | *L6* | *L1* | *L5*<br>*L10* | *L2* | *L5*<br>*L10* | *L3*<br>*L7*<br>*L8*<br>*L9*<br>*L11*<br>*L13* | *L12* | *L3*<br>*L7*<br>*L8*<br>*L9*<br>*L11*<br>*L13* |

FIG. 5I

|  | CD3 | CD4 | CD8 | CD11c | CD14 | CD16 | CD19 | CD45 | CD56 |
|---|---|---|---|---|---|---|---|---|---|
| Lymph Helper | X | X | | | | | | X | |
| Lymph Cytotoxic | X | | X | | | | | X | |
| Lymph B Cell | | | | | | | X | X | |
| Lymph NK | | | | | | X | | X | X |
| Monocyte | | X | | X | X | X | | X | |
| Dendritic | | | X | X | | X | | X | |
| | L4 | L6 | L1 | L10 | L2 | L5 | L3<br>L7<br>L9<br>L11<br>L13 | L12 | L8 |

FIG. 5J

|  | CD3 | CD4 | CD8 | CD11c | CD14 | CD16 | CD19 | CD45 | CD56 |
|---|---|---|---|---|---|---|---|---|---|
| Lymph Helper | X | X | | | | | | X | |
| Lymph Cytotoxic | X | | X | | | | | X | |
| *Lymph B Cell* | | | | | | | X | X | |
| Lymph NK | | | | | | X | | X | X |
| Monocyte | | X | | X | X | X | | X | |
| Dendritic | | | X | X | | X | | X | |
| | L4 | L6 | L1 | L10 | L2 | L5 | L3<br>L7<br>L9<br>L11<br>L13 | L12 | L8 |

*FIG. 5K*

|  | CD3 | CD4 | CD8 | CD11c | CD14 | CD16 | CD19 | CD45 | CD56 |
|---|---|---|---|---|---|---|---|---|---|
| Lymph Helper | X | X |  |  |  |  |  | X |  |
| Lymph Cytotoxic | X |  | X |  |  |  |  | X |  |
| Lymph B Cell |  |  |  |  |  |  | X | X |  |
| Lymph NK |  |  |  |  |  | X |  | X | X |
| Monocyte |  | X |  | X | X | X |  | X |  |
| Dendritic |  |  | X | X |  | X |  | X |  |
|  | L4 | L6 | L1 | L10 | L2 | L5 | L9 | L12 | L8 |

FIG. 5L

Results:

Marker CD3-Label 4
Marker CD4-Label 6
Marker CD8-Label 1
Marker CD11c-Label 10
Marker CD14-Label 2
Marker CD16-Label 5
Marker CD19-Label 9
Marker CD45-Label 12
Marker CD56-Label 8

SYSTEM AND METHOD FOR LABEL SELECTION

CROSS REFERENCE TO RELATED APPLICATIONS

This application is the national phase of PCT Application No. PCT/US2016/042083, filed on Jul. 13, 2016, which claims the benefit of U.S. Provisional Application No. 62/192,986, filed on Jul. 15, 2015, and U.S. Provisional Application No. 62/192,963, filed Jul. 15, 2015, each of which are incorporated herein by reference in their entirety. Furthermore, any and all priority claims identified in the Application Data Sheet, or any correction thereto, are hereby incorporated by reference under 37 C.F.R. § 1.57.

BACKGROUND OF THE INVENTION

Field of the Invention

This disclosure relates generally to the field of flow cytometry, and more particularly to methods for reducing error in sample analysis.

Description of the Related Art

Particle analyzers, such as flow and scanning cytometers, are analytical tools that enable the characterization of particles on the basis of optical parameters such as light scatter and fluorescence. In a flow cytometer, for example, particles, such as molecules, analyte-bound beads, or individual cells, in a fluid suspension are passed through a detection region in which the particles are exposed to an excitation light, typically from one or more lasers, and the light scattering and fluorescence properties of the particles are measured. Markers, such as cell surface protein components of cells the presence of which can serve as a distinguishing characteristic, may be recognized by reagents that include fluorescent dyes to facilitate detection, identification, and characterization. Each reagent can include a label, typically a fluorescent molecule or "dye," conjugated to a detector molecule that will selectively attach to a particular marker, for example, a monoclonal antibody. A multiplicity of different particles or components may be distinguished by using spectrally distinct fluorescent dyes to label the markers. In some implementations, a multiplicity of photodetectors are included in the analyzer. When a particle passes through the laser beam, time correlated pulses on forward scatter (FSC) and side scatter (SSC) detectors, and possibly also fluorescent emission detectors will occur. This is an "event," and for each event the magnitude of the detector output for each detector, FSC, SSC and fluorescence detectors is stored. The data obtained comprise the signals measured for each of the light scatter parameters and the fluorescence emissions.

Cytometers may further comprise components for storing the detector outputs and analyzing the data. For example, data storage and analysis may be carried out using a computer connected to the detection electronics. For example, the data can be stored logically in tabular form, where each row corresponds to data for one particle (or one event), and the columns correspond to each of the measured parameters. The use of standard file formats, such as an "FCS" file format, for storing data from a flow cytometer facilitates analyzing data using separate programs and/or machines. Using current analysis methods, the data typically are displayed in 2-dimensional (2D) plots for ease of visualization, but other methods may be used to visualize multidimensional data.

The parameters measured using a flow cytometer typically include FSC, which refers to the excitation light that is scattered by the particle along a generally forward direction, SSC, which refers to the excitation light that is scattered by the particle in a generally sideways direction, and the light emitted from fluorescent molecules in one or more channels (frequency bands) of the spectrum, referred to as FL1, FL2, etc., or by the name of the fluorescent dye that emits primarily in that channel. Different cell types can be identified by the scatter parameters and the fluorescence emissions resulting from labeling various cell proteins with dye-labeled antibodies.

Both flow and scanning cytometers are commercially available from, for example, BD Biosciences (San Jose, Calif.). Flow cytometry is described in, for example, Landy et al. (eds.), Clinical Flow Cytometry, Annals of the New York Academy of Sciences Volume 677 (1993); Bauer et al. (eds.), Clinical Flow Cytometry: Principles and Applications, Williams & Wilkins (1993); Ormerod (ed.), Flow Cytometry: A Practical Approach, Oxford Univ. Press (1997); Jaroszeski et al. (eds.), Flow Cytometry Protocols, Methods in Molecular Biology No. 91, Humana Press (1997); and Practical Shapiro, Flow Cytometry, 4th ed., Wiley-Liss (2003); all incorporated herein by reference. Fluorescence imaging microscopy is described in, for example, Pawley (ed.), Handbook of Biological Confocal Microscopy, 2nd Edition, Plenum Press (1989), incorporated herein by reference.

SUMMARY

In accordance with one aspect of the present invention, systems and methods are provided for flow cytometry experiments.

In one embodiment, a method for operating a flow cytometer having m detectors corresponding to m filter windows is provided. The method includes providing a label library including p labels having p corresponding emission spectra, providing a sample for testing having one or more cell populations having a total of n markers to be labeled, generating one or more spillover matrices having entries $S_{ij}$, wherein $S_{ij}$ corresponds to the response of a detector i to a label j, evaluating the condition numbers of the one or more spillover matrices for at least one selection of n or fewer of the p labels, selecting labels for at least some of the n markers based at least in part on the evaluating, and running a flow cytometry experiment with the flow cytometer using the selected labels.

In another embodiment, a system for flow cytometry is provided. The system includes a flow cytometer including m detectors corresponding to m filter windows, a label library including p labels having p corresponding emission spectra, a sample for testing using the flow cytometer, wherein the sample includes one or more cell populations having a total of n markers to be labeled, and a processing circuit. The processing circuit is configured to define one or more spillover matrices of dimensions m×q having entries Sij, wherein Sij corresponds to the response of a detector i to a label j, and wherein q≤n, evaluate condition numbers of the one or more spillover matrices for different selections of q of the p labels; and select labels for at least some of the n markers based at least in part on the evaluation of the condition numbers.

In another embodiment, a method for performing a flow cytometer experiment having a panel of fluorescent labels and a plurality of cell populations with a plurality of markers, each of the cell populations expressing a subset of the plurality of markers is provided. The method includes inputting to a computer system biological data assigning subsets of the plurality of markers to each of the plurality of cell populations, with the computer system, displaying a hierarchical visual representation of at least some of the plurality of cell populations, wherein the hierarchy is based at least in part on the subsets of the plurality of markers expressed by each of the cell populations, inputting, retrieving, or selecting marker density characteristics for at least some of the markers, inputting, retrieving, or selecting configuration data for a flow cytometer, inputting, retrieving, or selecting emission spectrum data for a plurality of labels, assigning labels to at least some of the markers, with the computer system, evaluating one or more of the assignments, with the computer system, displaying one or more results of the evaluating, optionally repeating the assigning labels, evaluating one or more of the assignments, and displaying one or more results, selecting a panel of reagents for use in a flow cytometry experiment, each reagent including one of the plurality of labels attached to a detector molecule, and running a flow cytometry experiment with the flow cytometer using the selected panel of reagents.

In another embodiment, a system for performing a flow cytometry experiment having a panel of fluorescent labels and a plurality of cell populations with a plurality of markers, each of the cell populations having a subset of the plurality of markers is provided. The system includes a flow cytometer having a plurality of detectors, a plurality of filters, and one or more excitation lasers configured to run a flow cytometry experiment, a computer system including a user interface configured to receive biological data assigning subsets of the plurality of markers to each of the plurality of cell populations, marker density characteristics for at least some of the markers, emission spectrum data for a plurality of labels, and an assignment of labels for at least some of the markers, and display a hierarchical visual representation of at least some of the cell populations, wherein the hierarchy is based at least in part on the subsets of the plurality of markers expressed by each of the cell populations, and one or more results of an evaluation of one or more of the assignments, a processing circuit configured to evaluate one or more of the assignments, and a memory storing label spectral characteristics for the plurality of labels and configuration data for the flow cytometer.

In another embodiment, a method for performing a flow cytometer experiment having a panel of fluorescent labels and a plurality of cell populations with a plurality of markers, each of the cell populations expressing a subset of the plurality of markers, is provided. The method can include inputting to a computer system biological data assigning subsets of the plurality of markers to each of the plurality of cell populations, inputting, retrieving, or selecting marker density characteristics for at least some of the markers, inputting, retrieving, or selecting configuration data for a flow cytometer; inputting, retrieving, or selecting emission spectrum data for a plurality of labels, assigning labels to at least some of the markers; with the computer system, evaluating one or more of the assignments based at least in part on one or more of label brightness, marker density, fluorescence spillover, and a condition number of one or more spillover matrices for at least one assignment of labels to at least some of the plurality of markers, the one or more spillover matrices having entries $S_{ij}$, wherein $S_{ij}$ corresponds to the response of a detector i to a label j, with the computer system, displaying one or more results of the evaluating; optionally repeating the assigning labels, evaluating one or more of the assignments, and displaying one or more results; selecting a panel of reagents for use in a flow cytometry experiment, each reagent comprising one of the plurality of labels attached to a detector molecule, and running a flow cytometry experiment with the flow cytometer using the selected panel of reagents.

In another embodiment, a system for performing a flow cytometry experiment having a panel of fluorescent labels and a plurality of cell populations with a plurality of markers, each of the cell populations having a subset of the plurality of markers, is provided. The system can include a flow cytometer having a plurality of detectors, a plurality of filters, and one or more excitation lasers configured to run a flow cytometry experiment and a computer system. The computer system can include a user interface configured to receive biological data assigning subsets of the plurality of markers to each of the plurality of cell populations, marker density characteristics for at least some of the plurality of markers, and emission spectrum data for a plurality of labels, a processing circuit configured to evaluate one or more of the assignments of labels to at least some of the plurality of markers based at least in part on one or more of label brightness, marker density, fluorescence spillover, and a condition number of one or more spillover matrices for at least one assignment of labels to at least some of the markers, the one or more spillover matrices having entries $S_{ij}$, wherein $S_{ij}$ corresponds to the response of a detector i to a label j, and a memory storing label spectral characteristics for the plurality of labels and configuration data for the flow cytometer.

BRIEF DESCRIPTION OF THE DRAWINGS

FIGS. 4A-J depict illustrative example of a series of display screens of a user interface in accordance with an illustrative embodiment of a process of performing a flow cytometer experiment FIGS. 5A-L depict an example of a label selection in accordance with an illustrative embodiment of the present invention.

DETAILED DESCRIPTION

The present invention provides systems and methods for performing flow cytometry experiments. Over the past several years, increases in the number of measurements made for the events of a flow cytometry experiment have been desired, and instrument manufacturers have developed flow cytometer instruments with detection systems and data analysis capabilities of increased complexity and performance. Advances in biochemistry have produced an increasingly large selection of fluorescent labels. Although these advances have made flow cytometry more useful than ever, harnessing that usefulness can still be a challenge. Label selection and instrument configuration are more complex, while at the same time experimental success is more dependent on appropriate experimental design. For example, the choice of fluorescent dyes used in a cytometry experiment is significant for the accuracy of the conclusions drawn from the data measured because the emission spectra from one fluorescent dye may overlap the detection bands of multiple detectors. Differences in relative brightness between labels and differences in the relative density of the markers labeled in an experiment can also affect the accuracy of event characterization.

Figure 1:
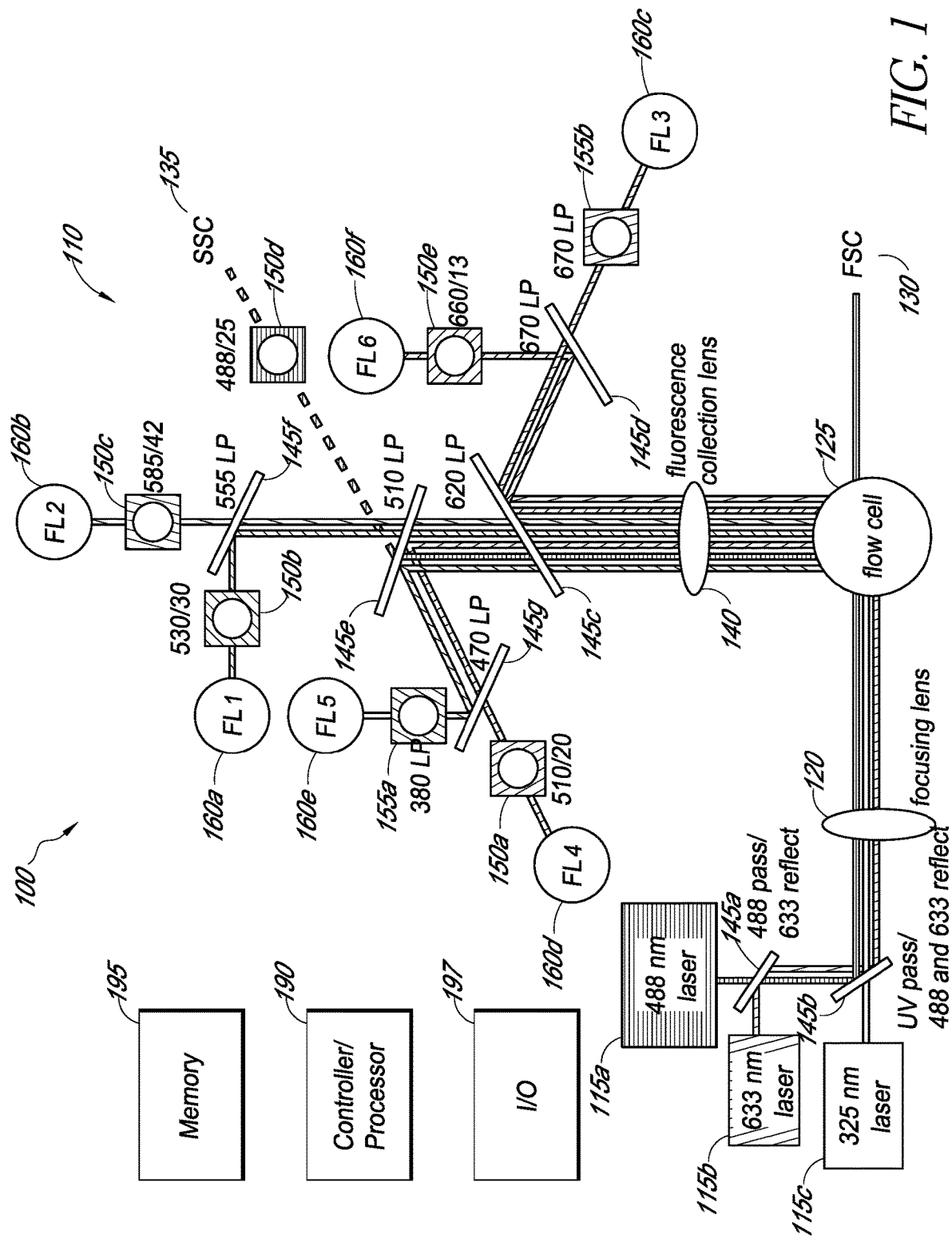
FIG. 1 depicts a flow cytometer in accordance with an illustrative embodiment of the present invention.

FIG. 1 shows a system 100 for flow cytometry in accordance with an illustrative embodiment of the present invention. The system 100 includes a flow cytometer 110, a controller/processor 190 and a memory 195. The flow cytometer 110 includes one or more excitation lasers 115a-c, a focusing lens 120, a flow chamber 125, a forward scatter detector 130, a side scatter detector 135, a fluorescence collection lens 140, one or more beam splitters 145a-g, one or more bandpass filters 150a-e, one or more longpass ("LP") filters 155a-b, and one or more fluorescent detectors 160a-f.

The excitation lasers 115a-c emit light in the form of a laser beam. The wavelengths of the laser beams emitted from excitation lasers 115a-c are 488 nm, 633 nm, and 325 nm, respectively, in the example system of FIG. 1. The laser beams are first directed through one or more of beam splitters 145a and 145b. Beam splitter 145a transmits light at 488 nm and reflects light at 633 nm. Beam splitter 145b transmits UV light (light with a wavelength in the range of 10 to 400 nm) and reflects light at 488 nm and 633 nm.

The laser beams are then directed to a focusing lens 120, which focuses the beams onto the portion of a fluid stream where particles of a sample are located, within the flow chamber 125. The flow chamber is part of a fluidics system which directs particles, typically one at a time, in a stream to the focused laser beam for interrogation. The flow chamber can comprise a flow cell in a benchtop cytometer or a nozzle tip in a stream-in-air cytometer.

The light from the laser beam(s) interacts with the particles in the sample by diffraction, refraction, reflection, scattering, and absorption with re-emission at various different wavelengths depending on the characteristics of the particle such as its size, internal structure, and the presence of one or more fluorescent molecules attached to or naturally present on or in the particle. The fluorescence emissions as well as the diffracted light, refracted light, reflected light, and scattered light may be routed to one or more of the forward scatter detector 130, the side scatter detector 135, and the one or more fluorescent detectors 160a-f through one or more of the beam splitters 145a-g, the bandpass filters 150a-e, the longpass filters 155a-b, and the fluorescence collection lens 140.

The fluorescence collection lens 140 collects light emitted from the particle-laser beam interaction and routes that light towards one or more beam splitters and filters. Bandpass filters, such as bandpass filters 150a-e, allow a narrow range of wavelengths to pass through the filter. For example, bandpass filter 150a is a 510/20 filter. The first number represents the center of a spectral band. The second number provides a range of the spectral band. Thus, a 510/20 filter extends 10 nm on each side of the center of the spectral band, or from 500 nm to 520 nm. Shortpass filters transmit wavelengths of light equal to or shorter than a specified wavelength. Longpass filters, such as longpass filters 155a-b, transmit wavelengths of light equal to or longer than a specified wavelength of light. For example, longpass filter 155a, which is a 670 nm longpass filter, transmits light equal to or longer than 670 nm. Filters are often selected to optimize the specificity of a detector for a particular fluorescent dye. The filters can be configured so that the spectral band of light transmitted to the detector is close to the emission peak of a fluorescent dye.

Beam splitters direct light of different wavelengths in different directions. Beam splitters can be characterized by filter properties such as shortpass and longpass. For example, beam splitter 145g is a 620 SP beam splitter, meaning that the beam splitter 145g transmits wavelengths of light that are 620 nm or shorter and reflects wavelengths of light that are longer than 620 nm in a different direction. In one embodiment, the beam splitters 145a-g can comprise optical mirrors, such as dichroic mirrors.

The forward scatter detector 130 is positioned slightly off axis from the direct beam through the flow cell and is configured to detect diffracted light, the excitation light that travels through or around the particle in mostly a forward direction. The intensity of the light detected by the forward scatter detector is dependent on the overall size of the particle. The forward scatter detector can include a photodiode. The side scatter detector 135 is configured to detect refracted and reflected light from the surfaces and internal structures of the particle, and tends to increase with increasing particle complexity of structure. The fluorescence emissions from fluorescent molecules associated with the particle can be detected by the one or more fluorescent detectors 160a-f. The side scatter detector 135 and fluorescent detectors can include photomultiplier tubes. The signals detected at the forward scatter detector 130, the side scatter detector 135 and the fluorescent detectors can be converted to electronic signals (voltages) by the detectors. This data can provide information about the sample.

One of skill in the art will recognize that a flow cytometer in accordance with an embodiment of the present invention is not limited to the flow cytometer depicted in FIG. 1, but can include any flow cytometer known in the art. For example, a flow cytometer may have any number of lasers, beam splitters, filters, and detectors at various wavelengths and in various different configurations.

In operation, cytometer operation is controlled by a controller/processor 190, and the measurement data from the detectors can be stored in the memory 195 and processed by the controller/processor 190. Although not shown explicitly, the controller/processor 190 is coupled to the detectors to receive the output signals therefrom, and may also be coupled to electrical and electromechanical components of the flow cytometer 100 to control the lasers, fluid flow parameters, and the like. Input/output (I/O) capabilities 197 may be provided also in the system. The memory 195, controller/processor 190, and I/O 197 may be entirely provided as an integral part of the flow cytometer 110. In such an embodiment, a display may also form part of the I/O capabilities 197 for presenting experimental data to users of the cytometer 100. Alternatively, some or all of the memory 195 and controller/processor 190 and I/O capabilities may be part of one or more external devices such as a general purpose computer. In some embodiments, some or all of the memory 195 and controller/processor 190 can be in wireless or wired communication with the cytometer 110. The controller/processor 190 in conjunction with the memory 195 and the I/O 197 can be configured to perform various functions related to the preparation and analysis of a flow cytometer experiment.

The system of FIG. 1 includes six different detectors that detect fluorescent light in six different wavelength bands (which may be referred to herein as a "filter window" for a given detector) as defined by the configuration of filters and/or splitters in the beam path from the flow cell 125 to each detector. Different fluorescent molecules used for a flow cytometer experiment will emit light in their own characteristic wavelength bands. The particular fluorescent labels used for an experiment and their associated fluorescent emission bands may be selected to generally coincide with the filter windows of the detectors. However, as more detectors are provided, and more labels are utilized, perfect correspondence between filter windows and fluorescent emission spectra is not possible. It is generally true that although the peak of the emission spectra of a particular fluorescent molecule may lie within the filter window of one particular detector, some of the emission spectra of that label will also overlap the filter windows of one or more other detectors. This may be referred to as spillover.

The I/O 197 can be configured to receive data regarding a flow cytometer experiment having a panel of fluorescent labels and a plurality of cell populations having a plurality of markers, each cell population having a subset of the plurality of markers. The I/O 197 can also be configured to receive biological data assigning one or more markers to one or more cell populations, marker density data, emission spectrum data, data assigning labels to one or more markers, and cytometer configuration data. Flow cytometer experiment data, such as label spectral characteristics and flow cytometer configuration data can also be stored in the memory 195. The controller/processor 190 can be configured to evaluate one or more assignments of labels to markers.

Figure 2:
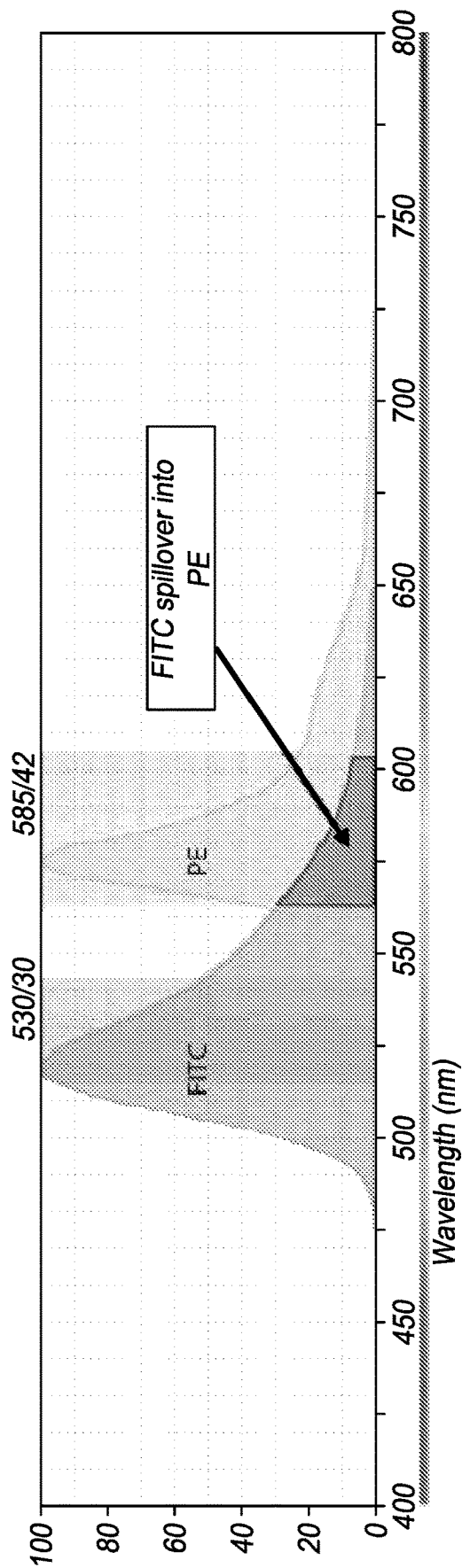
FIG. 2 depicts a graph showing examples of the emission spectra of labels and the filter windows of photodetectors in accordance with the present invention.

FIG. 2 shows an illustrative example of spillover caused by overlapping emissions spectra for different labels. FIG. 2 shows the emission spectra of markers labeled with FITC, represented by the curve extending from a wavelength of approximately 475 nm to 650 nm, and the filter window for a "FITC detector." One or more filters, such as bandpass filter 150b as depicted in FIG. 1, can be placed in front of the detector, limiting the range of wavelengths that can reach the detector, the range of wavelengths constituting a filter window. The filter window for the FITC detector is 530/30, meaning that the filter window extends from 515 nm to 545 nm. The FITC filter window is represented by the shaded rectangle extending from 515 nm to 545 nm. FIG. 2 also shows the emission spectra of markers labeled with PE, represented by the curve extending from approximately 525 nm to approximately 725 nm. One or more filters, such as bandpass filter 150c as depicted in FIG. 1, can be placed in front of the detector. The filter window for the PE detector is 585/42, meaning that the filter window extends from 564 nm to 606 nm. The PE filter window is represented by the shaded rectangle extending from 564 nm to 606 nm. FIG. 2 illustrates that a portion of the emissions spectra for FITC overlaps the filter window for the PE detector, labeled as "FITC spillover into PE." Therefore, some of the fluorescence emission of the FITC label is detected in the PE detector and measured along with the fluorescence emission of the PE label. Spillover can cause inaccurate conclusions to be drawn regarding the abundance of labels present on a particle. This problem can be especially acute for recent uses of flow cytometers as more labels and detectors are utilized, which reduces the separation of fluorescent peaks and filter windows. Given also the increasing number of fluorescent labels available (generally dozens of options are available to an experimenter), with a variety of peak wavelengths, emission intensities and energies, and spectral width characteristics, the variety of marker densities on cells being characterized, as well as in some cases selectable filter windows, it is very challenging to design a suitable set up for a flow cytometer experiment. A further complication is the autofluorescence of cells or other particles being characterized. This autofluorescence signal will also overlap one or more filter windows causing noise in the measurements. The autofluorescence noise signal can further be dependent on the type of particle/cell being interrogated.

Figure 3A:
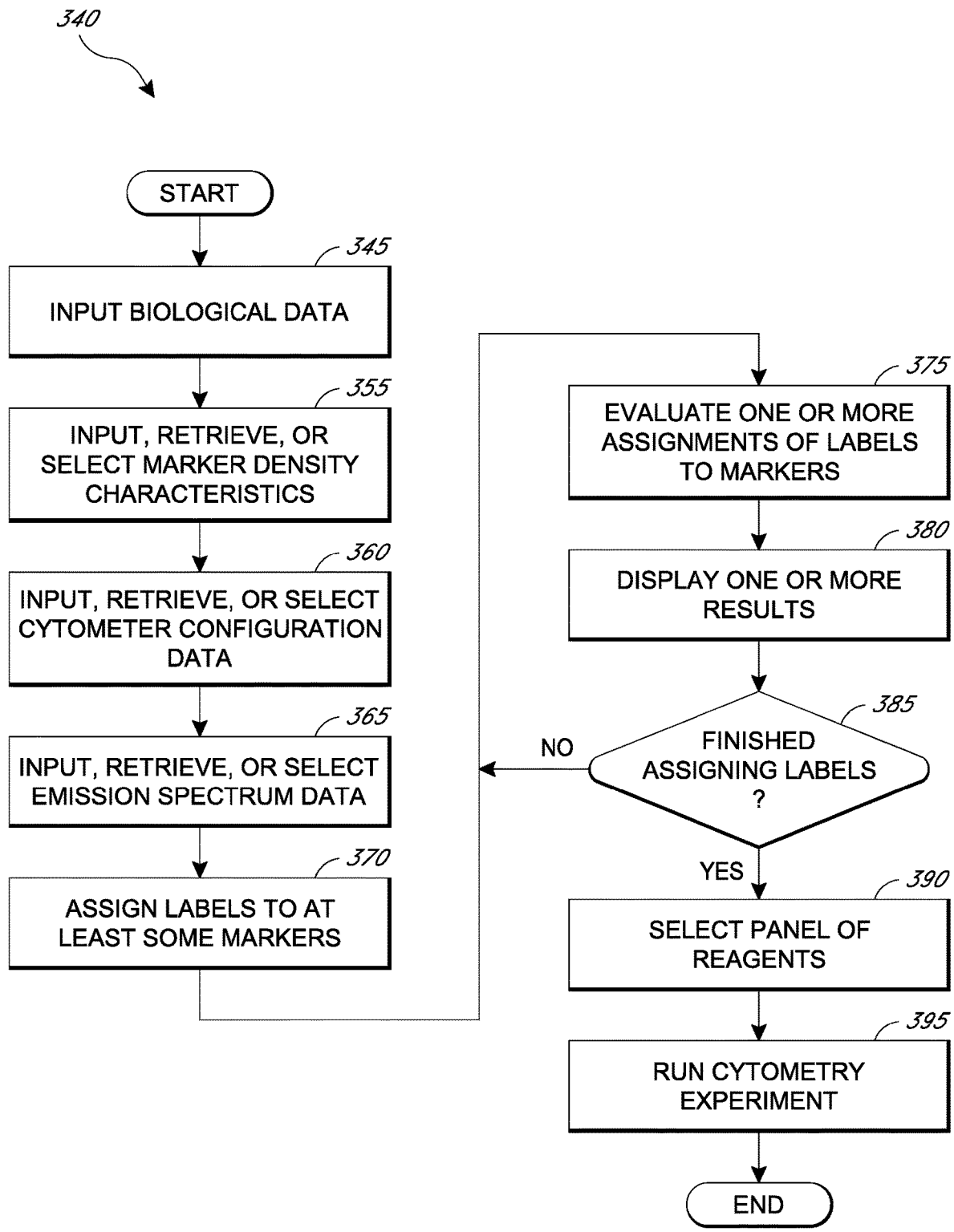
FIG. 3A depicts a flowchart of one embodiment of a process of performing a flow cytometer experiment in accordance with the present invention

FIG. 3A shows a flowchart of one embodiment of a process 340 of performing a flow cytometer experiment having a panel of p labels and a plurality of cell populations having n markers. Each of the cell populations can express a subset of the n markers. The process begins at a step 345, wherein biological data is input into a computer system assigning subsets of the n markers to each of the plurality of cell populations. Subsets of the n markers can be assigned using an I/O such as I/O 197 described with respect to FIG. 1. In some embodiments, inputting biological data includes inputting the identity of one or more of the n markers. Inputting biological data can further include inputting marker characteristics, such as for example, marker type and/or marker clone information. In some embodiments, biological data is retrieved from a memory or data base or selected from a set of options.

After the biological data is input into the computer system, the process 340 moves to a step 355, wherein marker density characteristics are input, retrieved, or selected for at least some of the n markers. In some embodiment, a marker density value in molecules per cell is input, retrieved, or selected. In other embodiments, the marker density characteristics include relative density classifications for co-expressed markers. For example, the marker density characteristics can include rankings of high, medium, and low. Alternatively, the marker density characteristics can include numerical rankings on a scale, such as, for example, from 1 to 3 or from 1 to 10. In one embodiment numerical values from 1 to 3 are input, retrieved, or selected, wherein a value of 1 indicates high marker density, a value of 2 indicates medium marker density, and a value of 3 indicates low marker density. In some embodiments, the marker density characteristics are input by a user using a computer system. In some embodiments, the marker density characteristics are selected from a set of possible marker density characteristics. In some embodiments, marker density characteristics are retrieved from a memory or database.

After the marker density characteristics are input, retrieved, or selected, the process 340 moves to a step 360, wherein configuration data for the flow cytometer is input, retrieved, or selected. The configuration data can include the model of the flow cytometer. The configuration data can also include data related to the lasers in the flow cytometer, for example, the color and wavelength of the lasers. The configuration data can also include the identities of the detectors in the flow cytometer and corresponding filter windows. In some embodiments, the configuration data is input by a user on a computer system. In some embodiments, the configuration data is selected from a set of options. In some embodiments, the configuration data is retrieved from a memory or database. In some embodiments, the configuration data is stored in a configuration library provided by the computer system.

After the configuration data is input, retrieved, or selected, the process 340 moves to a step 365, wherein emission spectrum data for the panel of p labels is input, retrieved, or selected. In some embodiments, the emission spectrum data includes a relative brightness value or ranking. In one embodiment, relative brightness can be ranked on a scale from 1 to 4 with 1 representing the lowest relative brightness and 4 representing the highest relative brightness. The emission spectrum data can also include a range of wavelengths over which one or more of the p labels emit. The emission spectrum data can also include ranges of wavelengths over which two or more of the p labels overlap. The emission spectrum data can include a graph or chart. The emission spectrum data can also include resolution impact data. Resolution impact data can include a percentage or range of percentages of loss of resolution due to the use of two or more of the p labels. In some embodiments, the emission spectrum data is input by a user on a computer system. In some embodiments, the emission spectrum data is selected by a user from a set of options. In some embodiments, emission spectrum data is retrieved from a memory or database. In some embodiments, the emission spectrum data is based at least in part on the configuration data. In some embodiments the panel of p labels for which emission spectra data is input, retrieved or selected can be input, retrieved, or selected based at least in part on the configuration data. For example, a list of available labels and corresponding data may be provided or retrieved based on wavelengths of the lasers in the flow cytometer and the filter windows of the detectors in the flow cytometer. In some embodiments, data for the panel of p labels can be retrieved from a label library provided by the computer system.

After the emission spectrum data is input, retrieved, or selected, the process 340 moves to a step 370, wherein n or fewer of the p labels are assigned to at least some of the n markers. The n or fewer of the p labels can be assigned by a user on a computer system or by a processor configured to assign labels.

After the n or fewer of the p labels are assigned, the process 340 moves to a step 375, wherein one or more of the assignments of n or fewer of the p labels are evaluated. The one or more assignments can be evaluated based on one or more of spillover, impact on the resolution in the detector, marker density, laser brightness, and condition number, described in further detail below. In some embodiments, an inverse relationship between marker density and label brightness may receive a favorable evaluation. For example, pairing a marker with a high marker density and a label with low brightness or a marker with low marker density and a label with high brightness will receive a favorable evaluation.

After the assignments are evaluated, the process 340 moves to a step 380, wherein one or more results of the evaluations are displayed. The results can be displayed on the flow cytometer or on an external device. In some embodiments, the evaluation results can include a warning if a label-marker assignment is evaluated as unfavorable. The results may also include a condition number.

After one or more results of the evaluations are displayed, the process 340 moves to decision step 385, wherein a decision is made whether the n or fewer of the p labels are finished being assigned or whether to repeat assigning the n or fewer of the p labels, evaluating one or more of the assignments, and displaying one or more results. If the n or fewer of the p labels are not finished being assigned, the process 340 returns to step 370.

If the n or fewer of the p labels are finished being assigned, the process 340 moves to a step 390, wherein a panel of reagents is selected. The panel of reagents can be selected from a set of commercially available options. In some embodiments, one or more reagents from the panel of reagents are ordered using the computer system.

After the panel of reagents is selected, the process 340 moves to a step 395, wherein a flow cytometry experiment is performed using the selected panel of reagents.

In some embodiments, the process 340 includes an additional step of displaying a visual representation of at least some of the plurality of cell populations. The visual representation can be hierarchical, wherein the hierarchy is based at least in part on the subsets of the n markers expressed by each of the cell populations. In some embodiments, the hierarchical visual representation is a modifiable population tree, described below with respect to FIG. 4C. In some embodiments, inputting biological data in step 345 can include creating a modifiable population tree.

In some embodiments, selection of labels can be performed based at least in part on reducing or minimizing spillover. To take spillover across multiple detectors for multiple labels into account, spectral overlap values may be characterized for all labels in all detectors through each respective filter window. At each detection event, the response of a given detector is the sum of the products of the overlap of the given detector filter window with each label multiplied respectively by the amount of each label present during the detection event. For a set of m detectors being used to detect n different labels during an experiment, a set of linear equations relating the observed m detector responses at the event with label abundances for each of the n labels at the event can be expressed as d=Ma, where d is an m×1 column vector of output measurements across all m detectors at the event, a is an n×1 column vector of label abundances of each of the n labels used in the experiment, and M is an m row×n column "spillover matrix." The spillover matrix M has entries $S_{ij}$, where $S_{ij}$ corresponds to the response of a detector i (where i runs from 1 to m) to a label j (where j runs from 1 to n). For example, the area of the "FITC spillover into PE" region of FIG. 2 is indicative of a spillover matrix entry where the detector i corresponds to the PE detector and the label j corresponds to the FITC label. When running an experiment, the detector outputs are measured for each event, and label abundances for each event are derived using the formula $a=M^{-1}d$, producing an abundance value for each label at each event based on the measured detector outputs at each event.

In an "ideal" experimental configuration where each detector is sensitive to emission from one and only one label, and no spillover from the emissions of other labels is present, the matrix M is orthogonal, and therefore exactly invertible into the matrix $M^{-1}$. As the one to one correspondence between detector and label is lost due to spillover, the farther from orthogonal the matrix M becomes. As M becomes less orthogonal, the same noise level in the detector measurements produces increasingly larger errors in the derived label abundances. To quantify how close the matrix M is to being orthogonal, the matrix M can be characterized by what is known as a "condition number." The condition number (CN) of a matrix is defined by the equation CN= (max σ)/(min σ), wherein CN is the condition number, max σ is the maximum singular value of M and min σ is the minimum singular value of M. An exactly orthogonal matrix has singular values that are all equal to each other, and therefore has a CN of 1, which is the smallest possible CN value for a matrix. Larger CN for the matrix M correlates to less orthogonality, and generally less accurate experimental results.

The cytometer experimental methods described herein can take the condition number of the matrix M or factors affecting spillover into account during the label assignment or selection process in an interactive, automated, or semi-automated manner that greatly assists users of flow cytometers to select labels and associate them with particular markers in a manner that optimizes the accuracy of the experimental results. In general, there may be m detectors, n markers, and p possible labels in a label library, with p greater than or equal to n. The process of "panel design" for a cytometer experiment involves selecting a unique one of the p labels for each one of the n markers.

In one possible implementation of label assignment using the CN of matrix M, every possible set of n labels from the library of p labels can be used to construct a matrix M from the spectral overlap of each label with each detector window. This will generate pCn matrices, and the condition number of each of these matrices can be computed. The set of n labels that is associated with a matrix M having the smallest CN can be selected as the label panel for the experiment. In this implementation, no particular assignment of individual ones of the n selected labels (corresponding to the lowest CN for the corresponding matrix M) to individual ones of the n markers is provided by the method. This assignment can be done in any manner, even randomly.

Although the above implementation can be used in some cases, it is generally beneficial to further consider the characteristics of the events that are expected by the experiment when these are known. For example, it is common to perform an experiment intended to distinguish and count different kinds of cells that are or might be present in a sample. Each different cell population may be known to express a different subset of the total n markers that may be present in the whole sample. In this situation, it is useful to consider subsets of the n markers corresponding to the different cell types as different groups, and evaluating the condition numbers of matrices M associated with the subsets separately. By doing this, for example in the manners described further below, events that are expected to contain larger numbers of different labels can be considered in a prioritized manner, which better optimizes the experimental results obtained. With these methods, not only are n labels from the library of p labels selected for the experiment, but they can be assigned to particular ones of the markers in a way that optimizes the experimental results for the events associated with cell types that are the most difficult to successfully characterize.

In some embodiments, n or fewer of the p labels can be assigned in step 330 by a process similar to that described below in steps 320-330 shown in FIG. 3B. In some embodiments, a combination of n or fewer of the p labels having the smallest condition number of the plurality of different combinations of n or fewer of the p labels is assigned.

Figure 3B:
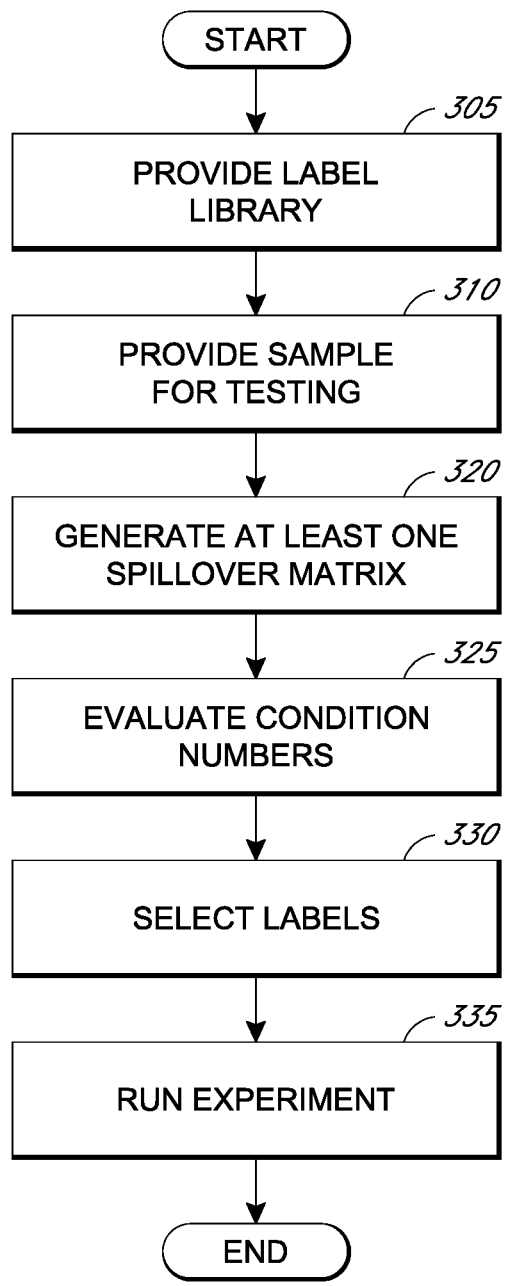
FIG. 3B depicts a flowchart of a process for selecting labels to use in a flow cytometry experiment in accordance with an illustrative embodiment of the present invention.

FIG. 3B depicts a flowchart of one embodiment of a process for selecting labels and performing a flow cytometry experiment based at least in part on condition numbers generated for a plurality of different combinations of labels. The process begins at a step 305, wherein a label library is provided, the label library having p labels with p corresponding emission spectra. The label library defines a plurality of fluorescent dyes available for use to label the markers of a particular sample.

After the label library is provided, the process moves to a step 310, wherein a sample for testing is provided. The sample can have one or more particle populations such as cells that in total exhibit n markers.

The process then moves to a step 320, wherein one or more spillover matrices are generated. The at least one spillover matrix can have entries $S_{ij}$, wherein $S_{ij}$ corresponds to the response of a detector i to a label j. As described above, the spillover matrices may be constructed from different selections of n or fewer labels of the p labels in the library.

After one or more spillover matrices are generated, the process moves to a step 325, wherein condition numbers for the one or more spillover matrices are evaluated for at least one selection of n or fewer of the p labels. The condition numbers can be evaluated to determine a selection of n or fewer of the p labels having the smallest condition number.

After the condition numbers are evaluated, the process moves to a step 330, wherein labels are selected for at least some of the n markers based at least in part on the evaluating of the condition numbers. The labels can be selected for at least some of the n markers so that the selection of labels is the selection having the smallest condition number. The selecting can also be based on relative brightness of the labels used, the relative density of the markers in a sample, the relative density of the markers in a particular cell population, and the identity of the markers in a particular cell population.

After the labels are selected, the process moves to a step 335, wherein a flow cytometer experiment is run using the selected labels on a flow cytometer, such as flow cytometer 110 depicted in FIG. 1.

In some embodiments, steps 320, 325, and 330 may be repeated for all populations in the sample. After repeating these steps separately for all populations, a complete assignment of n different labels to n different markers may be complete. Depending on the order that the different populations are run through steps 320, 325, and 330, a different set of n labels may be assigned to the n markers. In some embodiments steps 320, 325, and 330 can be repeated for all populations in the sample in descending order of the number of markers in each population. In some embodiments, steps 320, 325, and 330 can be repeated with the same population as the first population, and the remaining populations in different orders. The process 300 can comprise an additional step of summarizing all sets of labels selected when the populations are considered in different orders. The process 300 can include an additional step of selecting a set of labels from all sets of labels summarized having the lowest overall condition number. A flow cytometry experiment can then be run using the selection of labels from all sets of labels summarized having the lowest condition number.

In one embodiment of the process, a first population having q of the n markers is determined. The first population can be determined as the population having the largest number of markers of all populations in the experimental sample. After the first population is determined, a spillover matrix is generated for every possible combination of q labels, one label being selected from a set of labels available for each marker. Then, the condition numbers for each spillover matrix are evaluated. After the condition numbers are evaluated, a set of labels is selected for the markers in the first population having the lowest condition number. The process is then repeated for every other population in the sample. The labels available for each marker in the first population include every label in the label library. The labels available for markers in subsequent populations are limited by the sets of labels selected in previous populations. If a set of labels is selected for q markers in an earlier population, the labels available for any one of the q markers in a subsequent population are limited to the set of labels selected in the earlier population. The labels available for any of the n markers that were not part of the q markers in an earlier population are limited to the p labels not present in the set of labels selected for the q markers in the earlier population. In some embodiments, the process can be repeated with the same population used as the first population (which may advantageously be the population exhibiting the most markers), and the remaining populations selected in different orders. In some embodiments, all sets of labels determined using different population orders for the subsequent populations can be considered by evaluating different overall condition numbers, wherein the selection is the set of labels having the lowest overall condition number. A flow cytometry experiment can then be run using the selected set of labels.

The principles and methods described herein can be incorporated into a guided interactive design process for designing a flow cytometer experiment. An example of such a process is described below with respect to FIGS. 4A-J. A guided interactive design process can allow for a user to input, select, or retrieve data from a memory or database relating to various aspects of a flow cytometry experiment in order to design an experiment to meet their needs, and may further provide evaluations of the user inputs or selections during one or more segments of the process. A guided interactive design process can further allow the user to modify, redo, or revise any inputs or selections throughout the guided interactive design process to allow the user to explore multiple options and to receive multiple evaluations. In some embodiments, a guided interactive design process can further provide recommendations and/or information that may be relevant for making an input or selection prior to or during one or more steps of the interactive design process.

FIGS. 4A-J depict an illustrative example of a series of display screens of a user interface in accordance with an illustrative embodiment of a process of performing a flow cytometer experiment having a panel of fluorescent labels and a plurality of cell populations. The display screens of FIGS. 4A-J depict example data that is input, selected, or retrieved for an example flow cytometry experiment.

FIG. 4A depicts an example of a display screen 400 in accordance with an illustrative embodiment of a process of performing a flow cytometer experiment in which panel description information can be input, selected, or retrieved. The display screen 400 includes a name section 401 in which a name of a reagent panel can be input, selected, or retrieved. The display screen 400 also includes a description section 402 in which a description of the reagent panel can be input, selected, or retrieved.

Figure 4B:
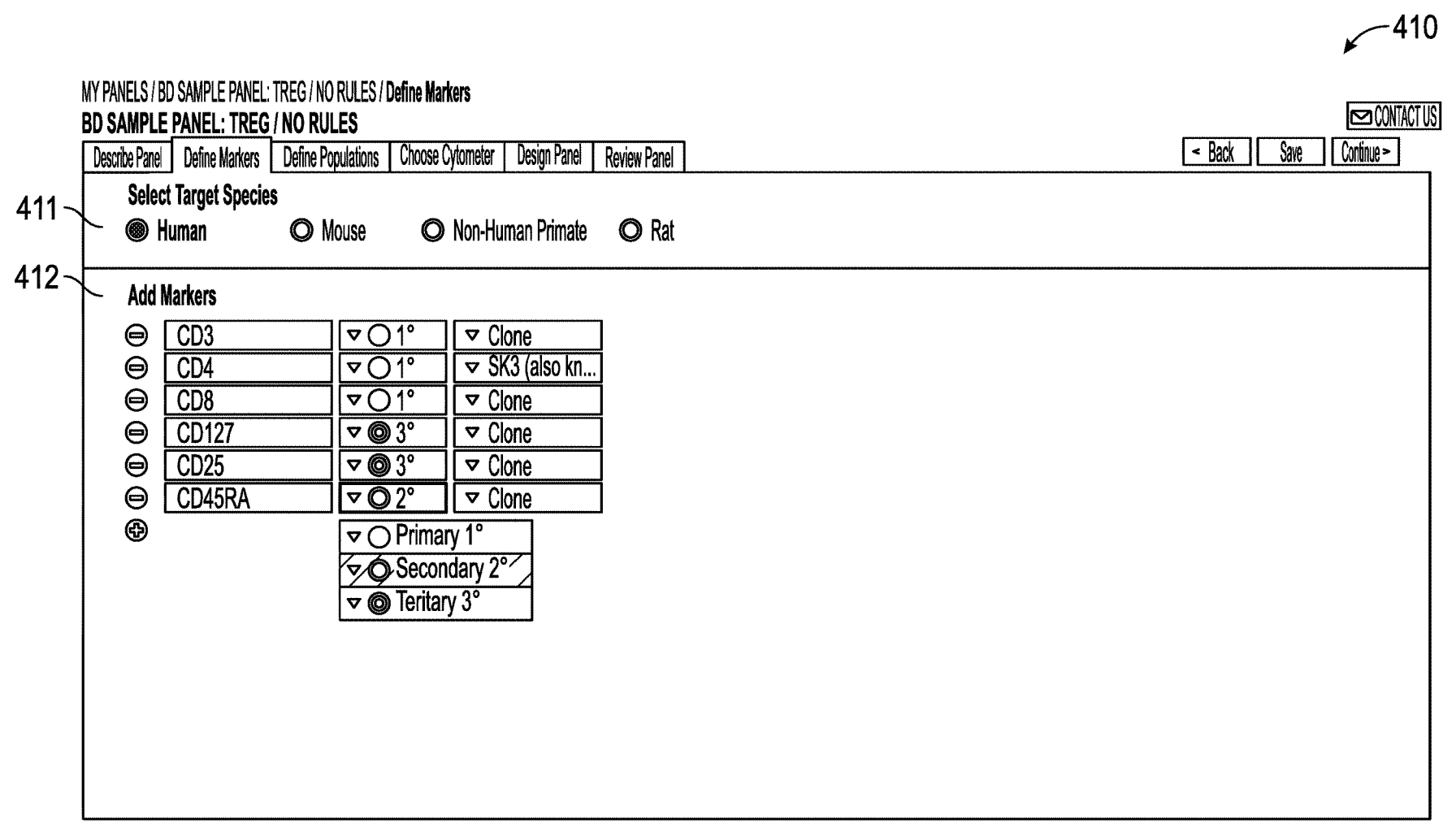

FIG. 4B depicts an example of a display screen 410 in accordance with an illustrative embodiment of a process of performing a flow cytometry experiment in which marker definition data can be input, selected, or retrieved. The display screen 410 includes a target species section 411 in which a target species, the species of cells used in the flow cytometer experiment, can be selected. In the example experiment depicted in FIG. 4B, the target species is Human. Display screen 410 also includes a marker selection section 412, in which marker specificity information can be input, selected or retrieved. The markers in the example experiment are CD3, CD4, CD8, CD45RA, CD127, and CD25. In the marker selection section 412, a marker type can be selected, input, or retrieved for each marker. Marker types can include primary, secondary, and tertiary. In FIG. 4B, primary, secondary, and tertiary markers represented using numerals 1, 2, and 3, respectively. Primary markers include markers that are generally well characterized and easily classified as positive or negative. Secondary markers include markers that are also generally well characterized and expressed at a higher density, often over a continuum, but may not be as well characterized as primary markers. Tertiary markers include markers that are generally expressed at low levels and can include uncharacterized markers. In the marker selection section 412 marker clone information can also be input, selected, or retrieved.

Figure 4C:
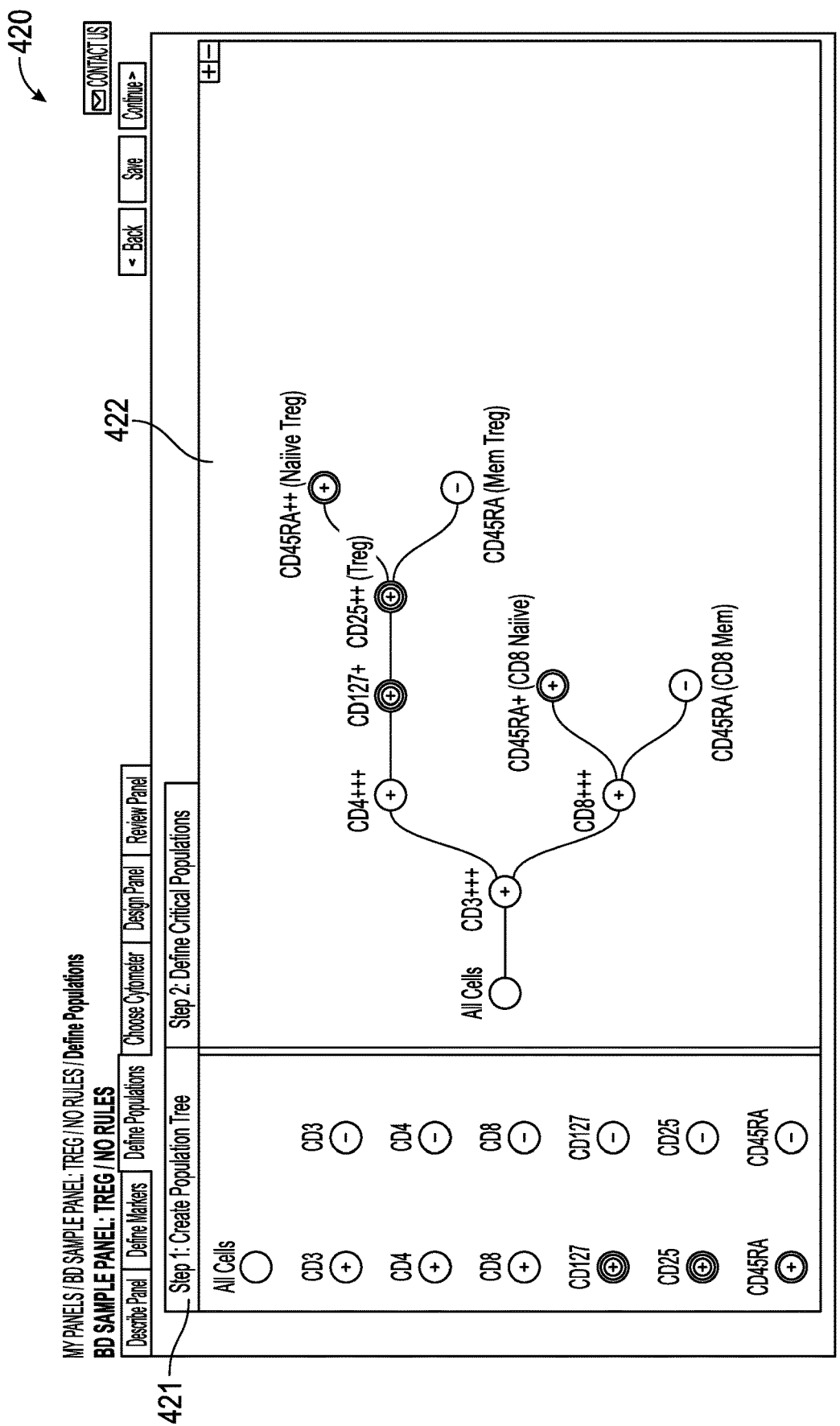

FIG. 4C depicts an example of a display screen 420 in accordance with an illustrative embodiment of a process of performing a flow cytometry experiment in which population data can be input, selected, or retrieved. Display screen 420 includes a markers section 421 having a manipulable icon with a plus for each marker input or selected using the marker definition screen and a manipulable icon with a minus for each marker input or selected using the marker definition screen. The manipulable icons can be selected and placed in a population tree section 422 to create a modifiable population tree. A manipulable icon with a plus indicates the presence of a marker in a population and a manipulable icon with a minus indicates the absence of the marker in the population. A population tree depicts each population based on the markers present in that population, beginning with a first population having a marker shared by each population in the population tree. The population tree includes branches from the first population tree to one or more subsequent populations. Each subsequent population can include a manipulable icon indicative of the presence or absence of a particular marker in the subsequent population. Each manipulable icon can include a plus in its interior to indicate the presence of a particular marker or a minus to indicate the absence of a particular marker. Each subsequent population can further include branches to one or more other subsequent populations. A particular population on the population tree is characterized by the marker, or lack of marker, indicated by the manipulable icon for that population, as well as each marker or lack of marker appearing on the chain of branches extending from the first population to the particular population. A population can be indicated by listing the markers and lack of markers that characterize that population. For example, a population having CD3, CD4, and CD127 markers can be labeled as CD3/CD4/CD127. In some embodiments, the order of the markers listed for a population can be indicative of the order in which the markers appear in the population tree.

In the example experiment depicted in FIGS. 4A-J, the first population includes CD3 markers and is indicated by the CD3+++ icon, wherein each + symbol is used to indicate an expression level of the marker as explained below. The first population branches in two different directions. In one direction is a population having CD8 and CD3 markers, the CD3+++/CD8+ population, indicated by the CD8+ icon. In the other direction is a population having CD4 and CD3 markers, the CD3+++/CD4+++ population, indicated by the CD4+++ icon. Following the CD3+++/CD4+++ population is a population having CD3, CD4, and CD127 markers, the CD3+++/CD4+++/CD127+ population, indicated by the CD127+ icon. Following the CD3+++/CD4+++/CD127+ population is a population having CD3, CD4, CD127, and CD25 markers, the CD3+++/CD4+++/CD127+/CD25++ population, indicated by the CD25++ icon. There are branches in two different directions from the CD3+++/CD4+++/CD127+/CD25++ population. In one direction is a population having CD3, CD4, CD127, CD25, and CD45RA markers, the CD3+++/CD4+++/CD127+/CD25++/CD45RA++ population, indicated by the CD45RA++ icon with a plus in its interior. In the other direction is a population having CD3, CD4, CD127, and CD25 markers, and not having the CD45RA marker, the CD3+++/CD4+++/

CD127+/CD25++/CD45RA− population, indicated by the CD45RA icon with a minus in its interior.

Figure 4D:
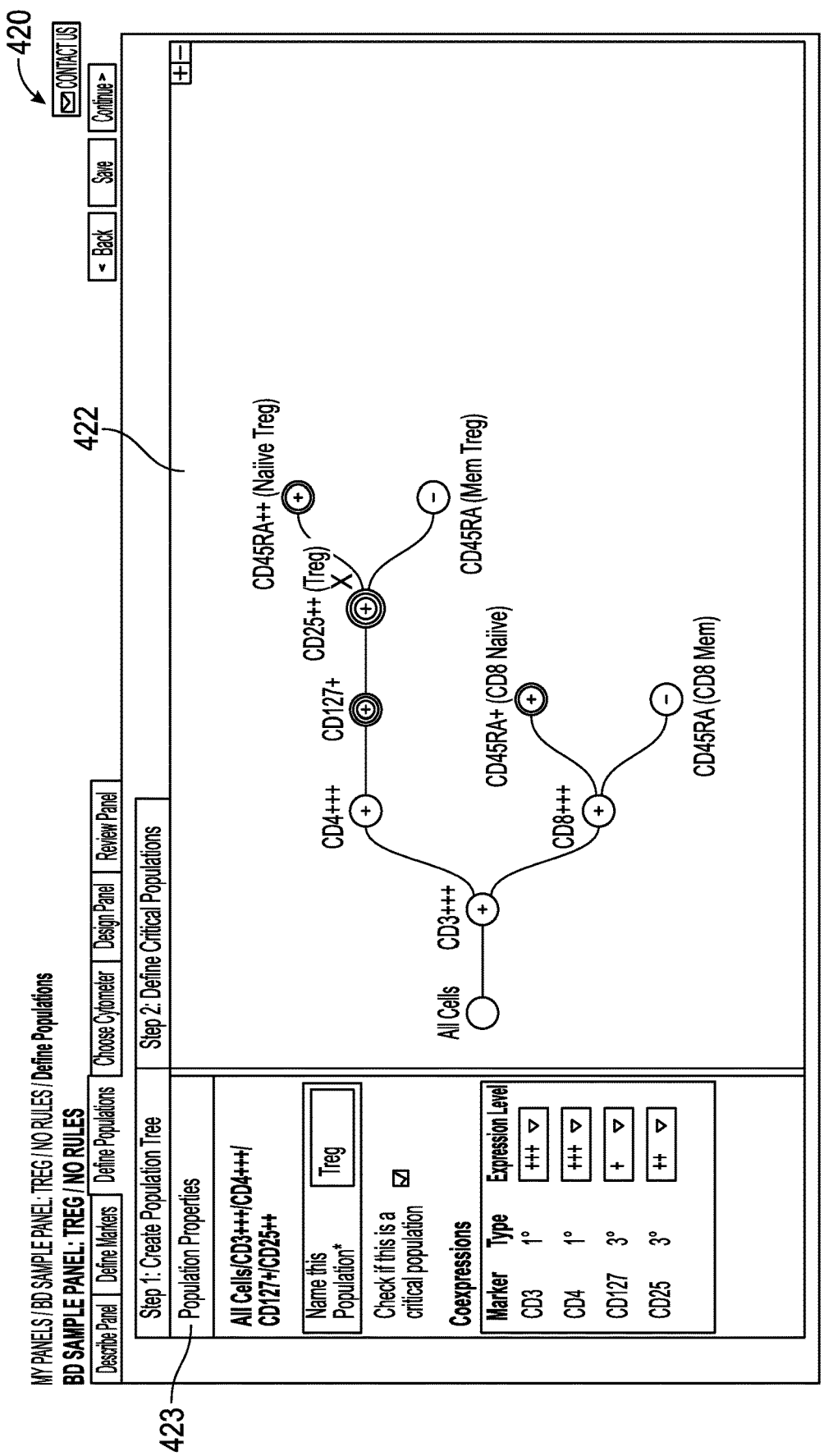

As depicted in FIG. 4D, the display screen 420 can further include a population properties section 423 in which information about a selected population can be input, selected, or retrieved. In some embodiments, the population properties section can be accessed when a particular population is input, selected, or retrieved. A population can be selected for the population properties section 423 by selection of the corresponding icon on the population tree. In the example depicted in FIG. 4D, the selected population is CD3+++/ CD4+/CD127+/CD25++. In the population properties section 423, a label or description can be added for a population. In the example, the label "Treg" has been added to the selected population. The labels or descriptions added in the population properties section 423 can appear in the population tree section 422. In the population properties section 423 a population can also be selected or designated as a population of interest. In the example, the CD3+++/CD4+/ CD127+/CD25++ has been designated as a population of interest, as indicated by the check mark next to the population of interest description in the population properties section 423. A population of interest can be displayed in the population tree section 422 by a graphic identifier. In the example, the population of interest is indicated in the population tree section 422 by a red "x" adjacent to the CD25++ icon on the modifiable population tree. The population properties section 423 also allows for an expression level to be input or selected for co-expressed markers. In the example, the expression level is shown as ranging from one plus to three pluses, where each plus indicates a higher expression level. The population properties section 423 can also indicate the marker type input, selected, or retrieved using the display screen 410 depicted in FIG. 4B.

Figure 4E:
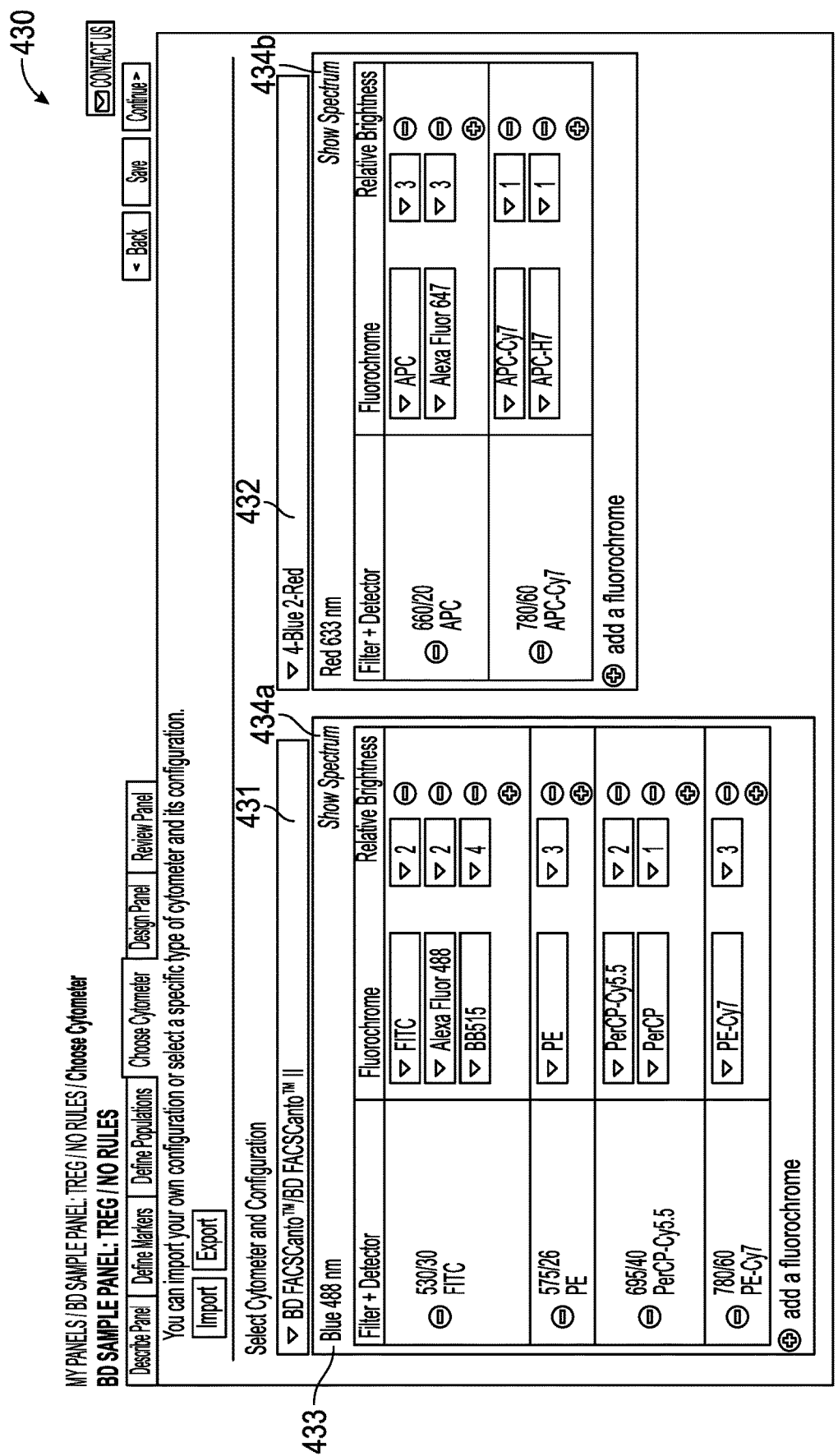

FIG. 4E depicts example of a display screen 430 in accordance with an illustrative embodiment of a process of performing a flow cytometry experiment in which cytometer and label data can be input, selected, or retrieved. The display screen 430 includes a cytometer selection section 431 in which a cytometer model can be input, selected, or retrieved. In the example experiment, the selected cytometer model is a BD FACSCanto™/BD FACSCanto™ II. The display screen 430 also includes a configuration selection section 432 in which a configuration for the selected cytometer can be input, selected, or retrieved. The configuration can include the number of lasers in the cytometer, the color of lasers in the cytometer, and the number of detectors for each laser in the cytometer.

The display screen 430 also includes a label data section 433 in which one or more filter windows associated with a laser of the selected configuration can be input, selected, or retrieved. For each filter window, a corresponding detector can be input, selected, or retrieved. For each detector, a fluorochrome, a fluorescent label, having an emission spectrum at least partially within the filter window corresponding to the detector can be input, selected, or retrieved. A relative brightness value or ranking can also be input, selected, or retrieved for each fluorochrome. In some embodiments, the filter window data, detector data, fluorochrome data, and relative brightness data is input by a user or selected from a set of options. In some embodiments, the filter window data, detector data, fluorochrome data, and relative brightness data is automatically populated from a cytometer library following selection of the cytometer model and configuration and may be modifiable. A filter window and corresponding detector can be input, selected, or retrieved, multiple times when more than one fluorochrome can be associated with the filter window.

Figure 4F:
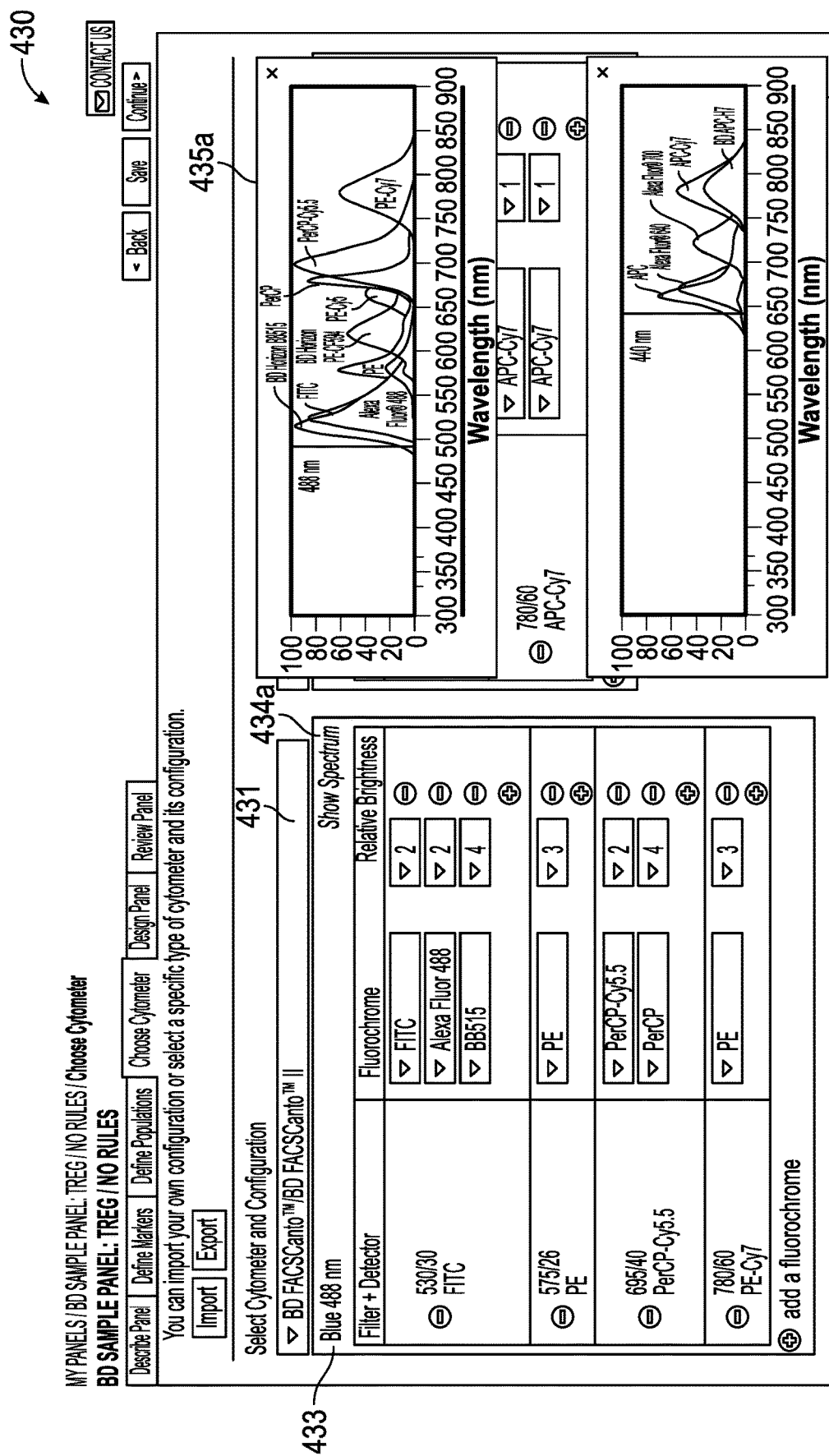

The display screen 430 further includes emission spectrum buttons 434a,b, one for each laser in the flow cytometer. Upon selection of an emission spectrum button 434a,b emission spectrum data can be displayed. FIG. 4F shows an example of a display screen 430 displaying emission spectrum data in accordance with an illustrative embodiment of a process of performing a flow cytometry experiment. In the example shown in FIG. 4E, the display screen 430 includes emission spectrum sections 435a,b including graphs that can show the emission spectra of each label input, selected, or retrieved in the label data section 433 for each laser. In some embodiments, the emission spectrum data is input by a user or selected from a set of options. In some embodiments, emission spectrum data is retrieved from a memory or database. In some embodiments, the emission spectrum data is retrieved from a label library.

Figure 4G:
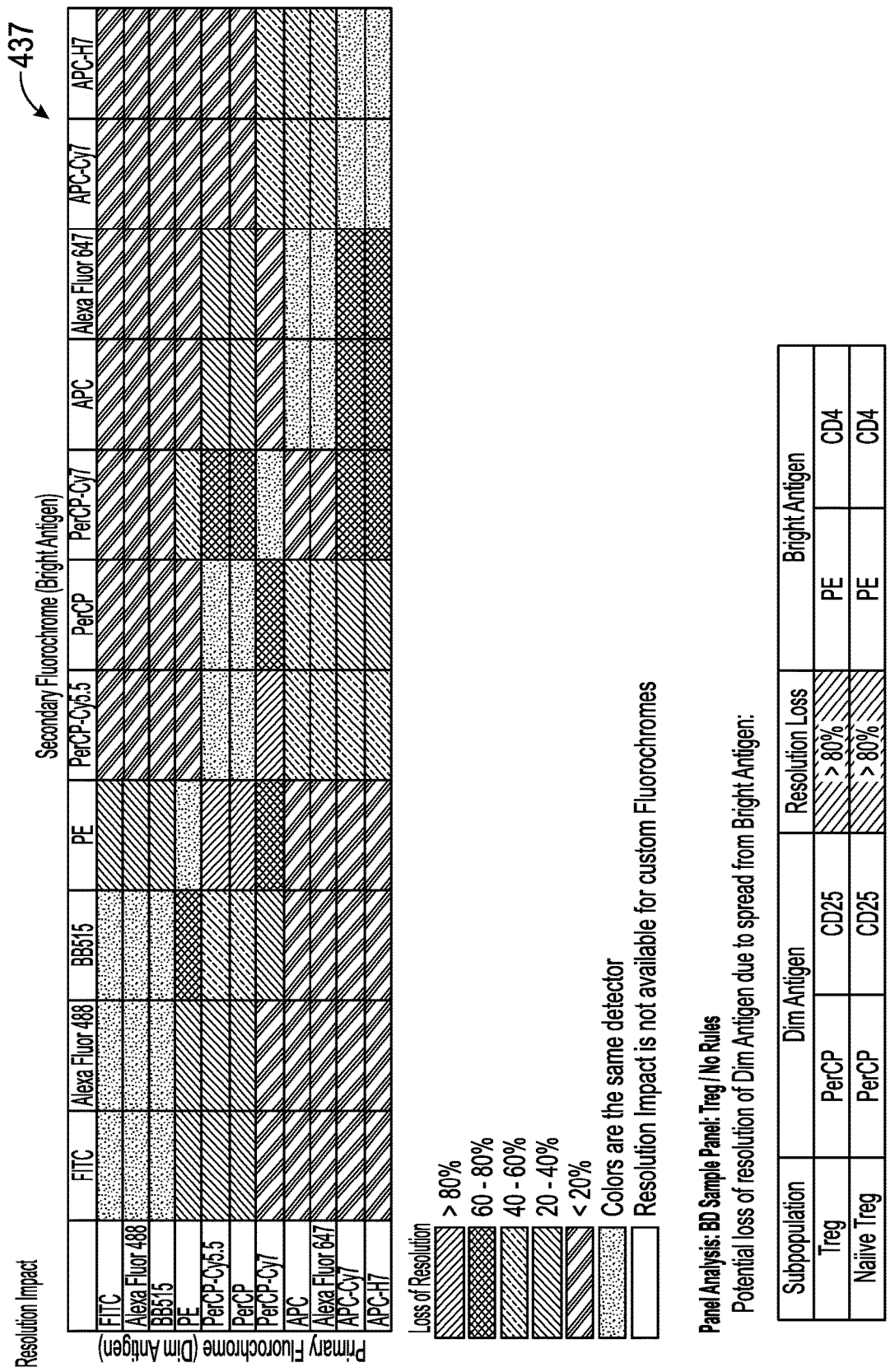

In some embodiments, the display screen 430 can further include a resolution impact button. Upon selection of the resolution impact button, resolution impact data can be displayed. FIG. 4G shows an example of a display screen displaying resolution impact data in accordance with an illustrative embodiment of a process of performing a flow cytometry experiment. In the example shown in FIG. 4G, the display screen includes a resolution impact section 437 including a table having a row and a column for each fluorochrome selected, input, or retrieved in the label data section 433. Each cell in the table shows a range of percent loss of resolution caused if the fluorochrome in the corresponding row is used as a primary fluorochrome and the fluorochrome in the corresponding column is used as a secondary fluorochrome. The percent loss in resolution can be determined based on the emission spectrum data. The percent loss in resolution can also be input, selected, or retrieved.

Although emission spectrum buttons is shown in FIG. 4E, and emission spectrum sections and resolution impact sections are shown in FIGS. 4F-G, it is contemplated that the display screen 430 can include buttons to provide for any visual representation indicating the effects of using two or more of the labels input, selected, or retrieved in label data section 433 together in a flow cytometer experiment. In some embodiments, a button may be provided to generate a condition number for one or more combinations of the labels input, selected, or retrieved in the label data section 433.

FIG. 4H depicts an example of a display screen 440 in accordance with an illustrative embodiment of a process of performing a flow cytometry experiment in which reagent panel design information can be input, selected, or retrieved. The panel design screen includes a co-expression section 441 showing the markers defined in the population tree depicted in display screen 420. The co-expression section 441 can also show marker density characteristics for the markers expressed in the population of interest. The density characteristics can be based on the expression level input, selected, or retrieved, in the population properties section 423 of the display screen 420. Markers having a high marker density can be indicated by an "H". Markers having a low marker density can be indicated by an "L". In the example experiment, the CD3 and CD4 markers have a high marker density and the CD127 and CD25 have low marker densities. CD45RA has a medium marker density.

The display screen 440 further includes a marker section 443 allowing for selection and manipulation of icons representing the markers defined in the population tree and a fluorochromes section 442 showing each fluorochrome input, selected, or retrieved in the label data section 433 of the display screen 430 along with the corresponding laser and relative brightness. Each maker in the markers section 443 can be assigned to a fluorochrome in the fluorochromes section 442. Assignment can be performed by manipulating an icon in the markers section 443 to associate the icon with a fluorochrome in the fluorochromes section 442. For example, an icon in the markers section 443 can be dragged and dropped on or adjacent to a fluorochrome in the fluorochrome section 442. Assignments are shown as visual indicators 444 showing a marker next to a fluorochrome to which it is paired. The visual indicators can include a selectable option, such as an "x" that can be selected to disassociate a particular marker with a particular fluorochrome. In one embodiment, when a marker is selected for assignment, a visual indicator will appear for each fluorochrome for which a commercial embodiment of a reagent including the selected marker and the fluorochrome is known. The display screen 440 can also include a notes section in which notes can be input. The display screen 440 can also include a resolution impact button 436 which allows for the generation of a resolution impact matrix, such as that shown above in FIG. 4G. The display screen 440 further includes an analyze panel button 445.

When the analyze panel button 445 is selected, a processor can analyze one or more of the marker-label assignments. The marker-label assignments can be evaluated based on one or more of spillover, impact on the resolution in the detector, marker density, laser brightness, and condition number. After the marker-label assignments are evaluated, one or more evaluation results can be displayed on the display screen 440. FIG. 4H shows an example of a display screen 440 displaying evaluation results in accordance with an illustrative embodiment of a process of performing a flow cytometry experiment. In the example shown in FIG. 4H, the display screen 440 shows exclamation points next to marker-label assignments that may be problematic. FIG. 4H also shows a text box 446 describing a result of the marker-label assignment evaluation. The text box 446 describes a mismatch of fluorochrome brightness and antigen resolution for the assignment of an APC-H7 label (shown in FIG. 4I) to the CD25 marker. In some embodiments, a text box 446, or other any other evaluation result, can be displayed in response to selecting the exclamation point next to a particular marker-label assignment. Although an exclamation point is shown in FIG. 445, it is contemplated that any visual icon can be used. In some embodiments, the display screen 440 can include a separate panel results section displaying the results of one or more marker-label evaluations. For example, the panel results section can display a warning that a marker with a low marker resolution is matched with a label with a low relative brightness. In some embodiments, the evaluation can be based on one or more of label brightness, marker density, fluorescence spillover, and a condition number of one or more spillover matrices for the label-marker assignments. In some embodiments, a condition number can be displayed in a panel results section for the label-marker assignments.

Figure 4I:
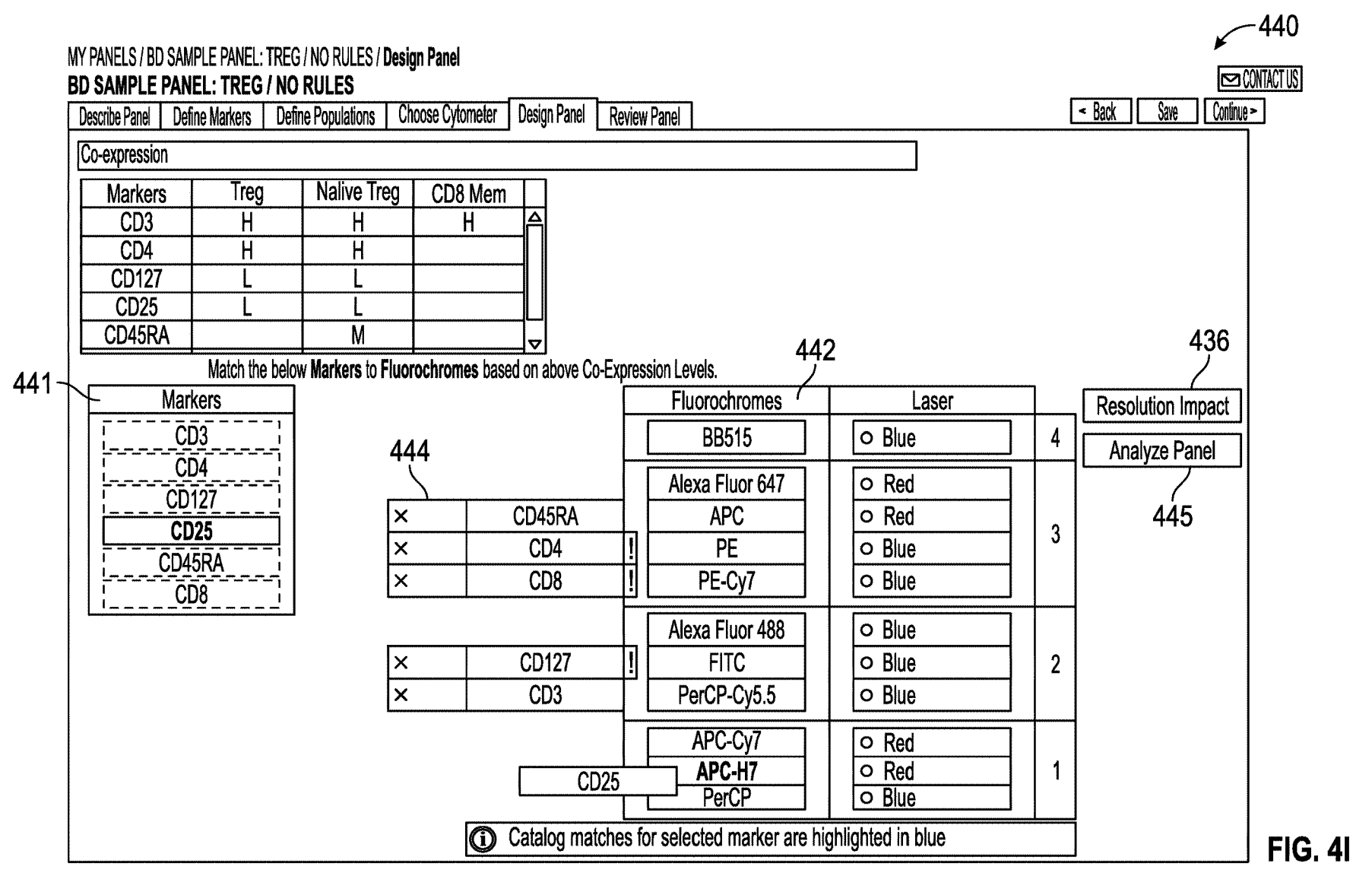

FIG. 4I shows an example of the CD25 marker being removed from the APC-H7 label. As depicted in FIG. 4I, the CD25 marker is selected and unassigned to a particular label. When a marker is selected and unassigned, one or more labels that are commercially available for the selected marker can be highlighted. FIG. 4I shows that the APC-H7 marker is highlighted.

FIG. 4J depicts an example of a display screen 450 in accordance with an illustrative embodiment of a process of performing a flow cytometry experiment in which commercially available reagents can be selected for each marker-label assignment. FIG. 4J shows a reagent selection section 453. The reagent selection section 453 includes commercially available reagents along with manufacturer information and catalog number information. Each commercially available reagent can include a manipulable icon to allow for selection of the commercially available reagent. In some embodiments, the display screen 450 can include an option to order one or more commercially available reagents. The reagent selection section 453 further includes an export button 454, which can export information regarding the experiment, such as selected reagents and/or marker-label assignments, to a memory, such as memory 195, a database, or a computer application. The display screen 450 can also include a notes section In accordance with an illustrative embodiment, the display screens 400, 410, 420, 430, 440, and 450 depicted in FIGS. 4A-J can be accessed in any order. The data in the display screens 400, 410, 420, 430, 440, and 450 can be modified at any time throughout the process of performing the flow cytometry experiment. Each display screen 400, 410, 420, 430, 440, and 450 can further include a save button, a continue button, or back button. Upon selection of the save button, the data input, selected, or retrieved in sections of the display screen can be stored in a memory, such as memory 195, or database. Upon selection of the continue button, a subsequent display screen of the user interface can be accessed. Upon selection of the back button, the user interface can return to a previous display screen.

As depicted in FIGS. 4A-J, the methods described herein allow for interactive design of a flow cytometry experiment. A user may input, select, or retrieve data relating to various aspects of a flow cytometry experiment, including biological data, which can include the identity of a plurality of markers for use in a cytometry experiment and marker characteristics, such as marker type and/or marker clone information, cytometer configuration data, and emission spectrum data. A user can also assign one or more labels to one or more markers and receive an evaluation and/or recommendation of one or more of the assignments of labels to markers. While the guided interactive design process may provide evaluations and recommendations for label-marker assignments, a user can choose to disregard or override any of the evaluations and recommendations. A user may also modify or revise any of the data input, selected or retrieved in designing the flow cytometry experiment at any point throughout the design process. Accordingly, a user can repeat assigning labels to markers and receiving evaluations of the assignments until the user is ready to select a preferred panel of reagents. A guided interactive design process as described herein can allow for customization and control of the design of a flow cytometer experiment while providing evaluations, recommendations, and other information that a user may find relevant.

Although the example depicted in FIGS. 4A-J provides an option for a user to select a panel of labels and assign those labels to a plurality of markers, it should be recognized that selection and assignment of labels markers can also be performed by a controller/processor, such as controller/processor 190 as shown in FIG. 1. For example, selection and assignment of labels can be performed based on condition numbers generated for different selections of available labels.

FIGS. 5A-L depict an illustrative embodiment of a process of selecting labels for a flow cytometry experiment based on condition numbers generated for different possible selections of labels. The selection may be performed using a process, such as the process depicted in FIG. 3B. In the example of FIG. 5A-L, one set of labels is selected by running through the populations in the order from most markers to least markers. The example experiment depicted in FIGS. 5A-L includes 6 populations: Lymph Helper, Lymph Cytotoxic, Lymph B cell, Lymph NK, Monocyte, and Dendritic, having a total of 9 markers: CD3, CD4, CD8, CD11c, CD14, CD16, CD19, CD45, and CD56. The label library for the experiment depicted in FIGS. 4A-L includes 13 labels, labels L1-L13. FIGS. 5A-L show a chart wherein the rows correspond to the populations and the columns correspond to the markers. An "x" in a box means that the marker represented in the corresponding column is present in the cell population in the corresponding row. The chart in FIGS. 5A-L also shows a list of labels available for each marker at the bottom of each column. In FIG. 5A labels are yet to be assigned. Any label could be paired with any available marker.

FIG. 5B depicts the result of determining a first cell population. In some embodiments, a first cell population can be determined by determining the cell population having the greatest number of markers. In FIG. 5B, the Monocyte population has been determined to be the first cell population. The Monocyte population includes five markers: CD4, CD11c, CD14, CD16, and CD45. After the first cell population is determined, all possible sets of labels for the five markers are determined without duplicates, one label from each bolded label list as shown in the chart on FIG. 5B, the label lists being a list of labels still available for a corresponding marker. Next, a specific set of five labels is selected that results in the lowest condition number of all possible sets of labels for the five markers. This selection can be performed by generating the spillover matrices as depicted in step 320 of FIG. 3B, evaluating condition numbers for the spillover matrices as depicted in step 335 of FIG. 3B, and selecting labels based at least in part on the evaluating as depicted in step 330 of FIG. 3B. In the example illustrated in FIGS. 5A-L, the set of 5 labels having the lowest possible condition number includes labels L2, L5, L6, L10, and L12.

FIG. 5C depicts the label lists for each marker after the selection of five labels was performed for the markers in the Monocyte population. The label lists for the markers in the Monocyte population include the 5 selected labels: L2, L5, L6, L10, and L12. Each of these five labels will be assigned to one of the markers in the Monocyte population. Therefore, these labels cannot be selected for any markers that are not present in the Monocyte population: markers CD3, CD8, CD19, and CD56. Thus, these five labels are removed from the label lists for all markers in the experiment that are not present in the Monocyte population. The label lists for all markers that are not present in the Monocyte population then includes labels L1, L3, L4, L7, L8, L9, L11, and L13.

FIG. 5D depicts the result of a step of determining a second cell population. In FIG. 5D, the Dendritic population has been determined. The Dendritic population includes four markers: CD8, CD11c, CD16, and CD45. After the Dendritic population is determined, all possible sets of labels for the four markers are determined without duplicates, one label from each bolded label list as shown in the chart of FIG. 5D. Next, a specific set of four labels is determined that results in the lowest condition number of all possible sets of labels for the four markers. In the example illustrated in FIGS. 5A-L, the set of four labels having the lowest possible condition number of all possible sets of labels for the four markers is L1, L5, L10, and L12.

FIG. 5E depicts the label lists for each marker after the selection of the four labels was performed for the Dendritic population. The four labels selected for the markers of the Dendritic population are removed from the label lists for all markers that are not in the Dendritic population. All labels that were not selected for the markers of the Dendritic population are removed from the label lists for the markers of the Dendritic population. FIG. 5E illustrates that as a result of this process, the only label available for marker CD8 is label L1, and label L1 is only available for the marker CD8.

FIG. 5F depicts the result of a step of determining a third cell population. In FIG. 5F, the Lymph helper population has been determined. The Lymph Helper population includes three markers: CD3, CD4, and CD45. After the Lymph Helper population is determined, all possible sets of labels for the three markers are determined without duplicates, one label from each bolded label list as shown in the chart of FIG. 5F. Next, a specific set of three labels is determined that results in the lowest condition number of all possible sets of labels for the three markers. In the example illustrated in FIGS. 5A-L, the set of three labels having the lowest possible condition number of all possible sets of labels for the three markers is L4, L6, and L12.

FIG. 5G depicts the label lists for each marker after the selection of the three labels was performed for the Lymph Helper population. The three labels selected for the markers of the Lymph Helper population are removed from the label lists for all markers that are not in the Lymph Helper population. All labels that were not selected for the markers of the Lymph Helper population are removed from the label lists for the markers of the Lymph Helper population.

FIG. 5H depicts the result of a step of determining a fourth cell population. In FIG. 5H, the Lymph Cytotoxic population has been determined. The Lymph Cytotoxic population includes three markers: CD3, CD8, and CD45. After the Lymph Cytotoxic population is determined, all possible sets of labels for the three markers are determined without duplicates, one label from each bolded label list as shown in the chart of FIG. 5H. Next, a specific set of three labels is determined that results in the lowest condition number of all possible sets of labels for the three markers. In the example illustrated in FIGS. 5A-L, only one label remains in each list: labels L4, L1, and L12. Consequently, there is no change in any of the label lists.

FIG. 5I depicts the result of a step of determining a fifth cell population. In FIG. 5I, the Lymph NK population has been determined. The Lymph NK population includes three markers: CD16, CD45, and CD56. After the Lymph NK population is determined, all possible sets of labels for the three markers are determined without duplicates, one label from each bolded label list as shown in the chart of FIG. 5I. Next, a specific set of three labels is determined that results in the lowest condition number of all possible sets of labels for the three markers. In the example illustrated in FIGS. 5A-L, the set of three labels having the lowest possible condition number of all possible sets of labels for the three markers is L5, L12, and L8.

FIG. 5J depicts the label lists for each marker after the selection of the three labels was performed for the Lymph NK population. The three labels selected for the markers of the Lymph NK population are removed from the label lists for all markers that are not in the Lymph NK population. All labels that were not selected for the markers of the Lymph NK population are removed from the label lists for the markers of the Lymph NK population.

FIG. 5K depicts the result of a step of determining a sixth cell population. In FIG. 5K, the Lymph B cell population has been determined. The Lymph B cell population includes two markers: CD19 and CD45. After the Lymph B cell population is determined, all possible sets of labels for the two markers are determined without duplicates, one label from each bolded label list as shown in the chart of FIG. 5K. Next, a specific set of two labels is determined that results in the lowest condition number of all possible sets of labels for the two markers. In the example illustrated in FIGS. 5A-L, the set of two labels having the lowest possible condition number of all possible sets of labels for the two markers is L9 and L12.

FIG. 5L depicts the label lists for each marker after the selection of the two labels was performed for the Lymph B cell population. The two labels selected for the markers of the Lymph B cell population are removed from the label lists for all markers that are not in the Lymph B cell population. All labels that were not selected for the markers of the Lymph B cell population are removed from the label lists for the markers of the Lymph B cell population. As a result of the process depicted in FIGS. 5A-L, each marker has only one label remaining in the corresponding label list. Therefore, those labels can be selected to the corresponding markers. Following the selection of labels, a flow cytometry experiment can be run using the selected labels.

In one embodiment, the process depicted in FIGS. 5A-L can be repeated with cell populations selected in different orders. Generally, it can be useful to maintain the population having the most markers as the first population, and vary the orders of the subsequent populations. This produces a set of label selections and assignments for each of the different orders of selection. The condition numbers for the overall matrix M can then be evaluated for each of the different label selections corresponding to the different population selection orders, and the label selection having the lowest overall condition number can be used in a flow cytometry experiment.

As used herein, the terms "determine" or "determining" encompass a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing, and the like.

As used herein, the terms "provide" or "providing" encompass a wide variety of actions. For example, "providing" may include storing a value in a location for subsequent retrieval, transmitting a value directly to the recipient, transmitting or storing a reference to a value, and the like. "Providing" may also include encoding, decoding, encrypting, decrypting, validating, verifying, and the like.

As used herein, a phrase referring to "at least one of" a list of items refers to any combination of those items, including single members. As an example, "at least one of: a, b, or c" is intended to cover: a, b, c, a-b, a-c, b-c, and a-b-c.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill in the art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The techniques described herein may be implemented in hardware, software, firmware, or any combination thereof. Such techniques may be implemented in any of a variety of devices such as general purposes computers, wireless communication devices, or integrated circuit devices having multiple uses including application in wireless communication device handsets and other devices. Any features described as modules or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials. The computer-readable medium may comprise memory or data storage media, such as random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable medium may be a non-transitory storage medium. The techniques additionally, or alternatively, may be realized at least in part by a computer-readable communication medium that carries or communicates program code in the form of instructions or data structures and that can be accessed, read, and/or executed by a computer, such as propagated signals or waves.

The program code may be executed by a processor, which may include one or more processors, such as one or more digital signal processors (DSPs), general purpose microprocessors, an application specific integrated circuits (ASICs), field programmable logic arrays (FPGAs), or other equivalent integrated or discrete logic circuitry. Such a processor may be configured to perform any of the techniques described in this disclosure. A general purpose processor may be a microprocessor; but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Accordingly, the term "processor," as used herein may refer to any of the foregoing structure, any combination of the foregoing structure, or any other structure or apparatus suitable for implementation of the techniques described herein. In addition, in some aspects, the functionality described herein may be provided within dedicated software modules or hardware modules configured for encoding and decoding, or incorporated in a combined video encoder-decoder (CODEC).

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

Various embodiments of the invention have been described. These and other embodiments are within the scope of the following claims.

What is claimed is:

1. A method for performing a flow cytometer experiment having a panel of fluorescent labels and a plurality of cell populations with a plurality of markers, each of the cell populations expressing a subset of the plurality of markers, comprising:
   inputting to a computer system biological data assigning subsets of the plurality of markers to each of the plurality of cell populations;
   inputting, retrieving, or selecting marker density characteristics for at least some of the markers;
   inputting, retrieving, or selecting configuration data for a flow cytometer;
   inputting, retrieving, or selecting emission spectrum data for a plurality of labels;
   assigning labels to at least some of the markers;
   generating one or more spillover matrices having entries $S_{ij}$;
   with the computer system, evaluating a condition number of one or more spillover matrices for the assigned labels to at least some of the plurality of markers, the one or more spillover matrices having entries $S_{ij}$, wherein $S_{ij}$ corresponds to the response of a detector i to a label j wherein generating the spillover matrices and evaluating the condition numbers are performed separately for each cell population;
   with the computer system, displaying one or more results of the evaluating;
   optionally repeating the assigning labels, evaluating one or more of the assignments, and displaying one or more results;
   selecting a panel of reagents for use in a flow cytometry experiment based on the generated spillover matrices and evaluated condition numbers for the spillover matrices, each reagent comprising one of the plurality of labels attached to a detector molecule; and
   running a flow cytometry experiment with the flow cytometer using the selected panel of reagents.

2. The method of claim 1, wherein assigning labels to at least some of the markers is performed manually.

3. The method of claim 1, wherein the plurality of labels comprises p labels having p corresponding emission spectra, wherein the plurality of markers comprises a total of n markers to be labeled, wherein assigning labels to at least some of the markers comprises:
   generating, one or more spillover matrices having entries $S_{ij}$, wherein $S_{ij}$ corresponds to the response of a detector i to a label j;
   evaluating the condition numbers of the one or more spillover matrices for at least one selection of n or fewer of the p labels; and
   selecting labels for at least some of the n markers based at least in part on the evaluating.

4. The method of claim 3, further comprising determining a first population of the sample having the greatest number of markers of all of the cell populations within the sample, wherein evaluating the condition numbers of the spillover matrices for at least one selection of n or fewer of the p labels is first performed for different combinations of a number of the p labels corresponding to the number of markers of the first population.

5. The method of claim 3, wherein assigning labels comprises determining a subset of the labels having the lowest condition number for the first population.

6. The method of claim 4, wherein generating the spillover matrices for the assignment of labels, evaluating the condition numbers, and selecting labels are performed sequentially for one or more of the remaining cell populations in descending order of the number of markers in each cell population, wherein the labels available for a marker in a population are limited to the labels previously for populations having the same marker.

7. The method of claim 6, further comprising repeating generating the spillover matrices for the assignment of labels, evaluating the condition numbers, and selecting labels sequentially for one or more of the remaining cell populations with every cell population used as a first remaining cell population in the sequence.

8. The method of claim 3, further comprising summarizing all selections of labels, and wherein selecting labels comprises determining the selection of labels having the smallest overall condition number.

9. The method of claim 1, further comprising, with a computer system, displaying a hierarchical visual representation of at least some of the one or more cell populations, wherein the hierarchy is based at least in part on the subsets of the markers expressed by each of the one or more cell populations.

10. The method of claim 9, wherein the displaying a hierarchical visual representation of at least some of the plurality of cell populations comprises providing a modifiable population tree.

11. The method of claim 1, further comprising optionally repeating the assigning labels and evaluating one or more assignments.

12. The method of claim 1, wherein the inputting, retrieving, or selecting marker density characteristics comprises inputting, retrieving, or selecting relative density classifications for co-expressed markers.

13. The method of claim 1, further comprising inputting, retrieving, or selecting relative brightness classifications for the plurality of labels.

14. The method of claim 1, wherein the configuration data for the flow cytometer comprises one or more of excitation laser specifications, detector specifications, filter specifications, and filter window specifications.

15. The method of claim 1, further comprising selecting one or more reagents and with the computer system, ordering the one or more reagents.

* * * * *